(12) United States Patent
Goutayer et al.

(10) Patent No.: US 11,266,577 B2
(45) Date of Patent: Mar. 8, 2022

(54) STABLE EMULSIONS OF POLYMER-SHELL DROPS

(71) Applicant: CAPSUM, Marseilles (FR)

(72) Inventors: Mathieu Goutayer, Saint Malo (FR); Amélie Pujol, Marseilles (FR)

(73) Assignee: CAPSUM, Marseilles (FR)

( * ) Notice: Subject to any disclaimer, the term of this patent is extended or adjusted under 35 U.S.C. 154(b) by 0 days.

(21) Appl. No.: 15/761,015

(22) PCT Filed: Sep. 16, 2016

(86) PCT No.: PCT/EP2016/071924
§ 371 (c)(1),
(2) Date: Jul. 9, 2018

(87) PCT Pub. No.: WO2017/046299
PCT Pub. Date: Mar. 23, 2017

(65) Prior Publication Data
US 2018/0333340 A1 Nov. 22, 2018

(30) Foreign Application Priority Data
Sep. 18, 2015 (FR) ....................................... 1558847

(51) Int. Cl.
| | |
|---|---|
| *A61K 8/06* | (2006.01) |
| *A61Q 1/02* | (2006.01) |
| *A61K 8/81* | (2006.01) |
| *A61Q 19/08* | (2006.01) |
| *A61K 8/898* | (2006.01) |
| *A61K 8/11* | (2006.01) |
| *B01F 17/54* | (2006.01) |
| *B01J 13/10* | (2006.01) |
| *B01F 17/00* | (2006.01) |

(52) U.S. Cl.
CPC .............. *A61K 8/062* (2013.01); *A61K 8/11* (2013.01); *A61K 8/8147* (2013.01); *A61K 8/898* (2013.01); *A61Q 1/02* (2013.01); *A61Q 19/08* (2013.01); *B01F 17/005* (2013.01); *B01F 17/0071* (2013.01); *B01J 13/10* (2013.01); *A61K 2800/5424* (2013.01); *A61K 2800/5426* (2013.01); *A61K 2800/594* (2013.01)

(58) Field of Classification Search
CPC ........ A61K 8/062; A61K 8/11; A61K 8/8147; A61K 8/898; A61K 2800/5424; A61K 2800/5426; A61K 2800/594; A61Q 1/02; A61Q 19/08; B01F 17/005; B01F 17/0071; B01J 13/10
See application file for complete search history.

(56) References Cited

U.S. PATENT DOCUMENTS

| | | | | |
|---|---|---|---|---|
| 6,042,815 A | * | 3/2000 | Kellner | .................. A61K 8/042 424/400 |
| 2003/0198654 A1 | * | 10/2003 | Palazzolo | .............. A61K 8/678 424/401 |
| 2008/0311064 A1 | * | 12/2008 | Lei | .......................... A61K 8/11 424/70.11 |
| 2012/0282309 A1 | * | 11/2012 | Dihora | ..................... A61K 8/11 424/401 |
| 2013/0129648 A1 | * | 5/2013 | Nguyen | .................... A61Q 5/12 424/59 |
| 2014/0045949 A1 | | 2/2014 | Goutayer et al. | |
| 2016/0250611 A1 | | 9/2016 | Goutayer et al. | |
| 2016/0256364 A1 | * | 9/2016 | Dihora | ..................... A61K 8/11 |
| 2016/0262990 A1 | | 9/2016 | Goutayer et al. | |

FOREIGN PATENT DOCUMENTS

| | | | | |
|---|---|---|---|---|
| DE | 19933452 A1 | * | 2/2000 | ............ A61K 8/042 |
| FR | 2 792 190 A1 | | 10/2000 | |
| FR | 3 012 050 A1 | | 4/2015 | |
| JP | H02-295912 A | | 12/1990 | |
| WO | 2012/120043 A2 | | 9/2012 | |
| WO | 2015/055839 A1 | | 4/2015 | |
| WO | 2015/0557748 A1 | | 4/2015 | |
| WO | 2015/148892 A1 | | 10/2015 | |

OTHER PUBLICATIONS

Carbopol 1342 Polymer. Product Specification. Lubrizol. 1997. 1 page. (Year: 1997).*
Sharipova et al. The Use of Polymer and Surfactants for the Microencapsulation and Emulsion Stabilization (Review). Colloids Interfaces 2017, 1, 3. 15 pages. (Year: 2017).*
International Search Report dated Oct. 26, 2016 for the related International Application No. PCT/EP2016/071924.
French Search Report dated Feb. 8, 2016 for the related French Application No. FR 15 58847.

* cited by examiner

*Primary Examiner* — Robert A Wax
*Assistant Examiner* — Olga V. Tcherkasskaya
(74) *Attorney, Agent, or Firm* — Pearne & Gordon LLP

(57) ABSTRACT

An emulsion comprising a continuous aqueous phase and a dispersed fatty phase in the form of drops, or conversely, wherein the drops comprise a shell formed of at least one anionic polymer comprising at least one carboxylic acid function and at least one cationic polymer comprising at least two amine functional groups, wherein the quantity of amine functional groups provided by the cationic polymer in the fatty phase is between 0.2 µmol and 10.5 µmol per gram of fatty phase.

17 Claims, 4 Drawing Sheets

STABLE EMULSIONS OF POLYMER-SHELL DROPS

Figure 1:
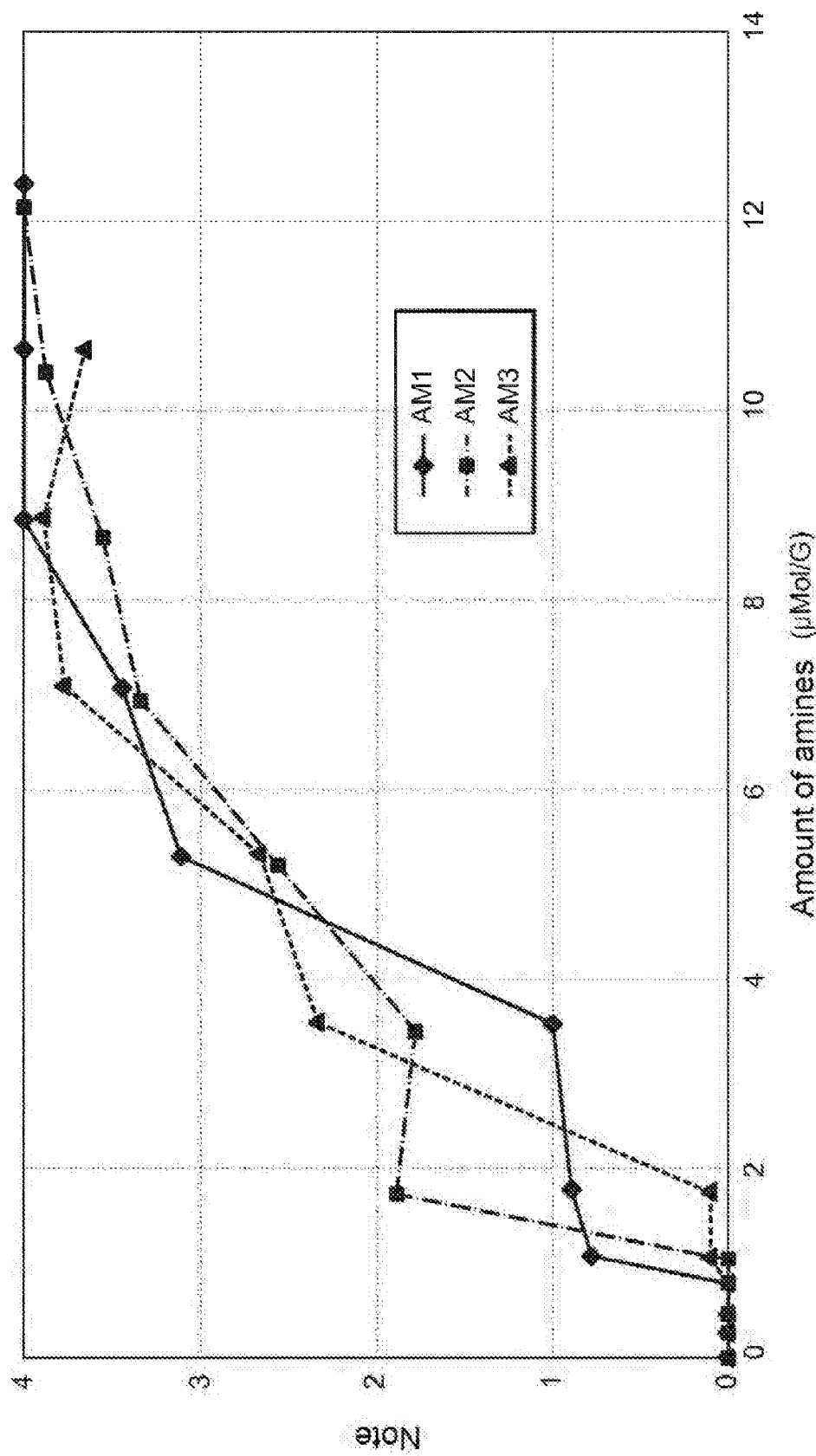

This invention relates to stable emulsions of the water-in-oil or oil-in-water type, in particular for a cosmetic application. It also relates to compositions, especially cosmetic, comprising the emulsions. It also relates to the cosmetic use of the emulsions and/or compositions, especially for make-up and/or the care of keratin materials, especially the skin.

In the cosmetic field, there are many types of compositions, especially in the form of emulsions, that are, in particular, stabilized by surfactants.

However, the presence of surfactants does not allow the consideration of all possible formulations. Moreover, because of their potentially irritating effects, users are increasingly looking for cosmetic products free of such surfactants. In addition, users of cosmetic compositions are increasingly looking for compositions that are easy to apply to the skin and that have satisfactory cosmetic properties, especially in terms of texture. Finally, the provision of emulsions obtained by simple preparation methods remains a constant objective.

WO/2012/120043 describes a method for forming drops stabilized by complex biphasic coacervation, in particular by microfluidics. This simple method leads to the formation of a plurality of stable drops stabilized by a very thin shell.

Nevertheless, the development of emulsions with improved characteristics, particularly in terms of mechanical strength and coalescence, remains a constant objective.

The present invention thus aims to provide a kinetically stable emulsion, for example at room temperature or at elevated temperature, especially up to 50° C.

For the purposes of the present invention, the term "kinetically stable" is understood to mean an emulsion that is stable over time, i.e. for which a visual homogeneity of the dispersed phase in the continuous phase remains satisfactory or, in other words, for which no phase shift is observed.

The present invention also aims to provide an emulsion having improved properties in terms of mechanical strength, allowing the emulsion, in particular, to withstand shearing or fragmentation of the drops, for example during the industrialization or transport of the emulsion or compositions, or the cosmetic products containing it.

Another object of the present invention is to provide an emulsion having improved properties in terms of resistance to coalescence.

The present invention further aims to provide a cosmetic emulsion having satisfactory cosmetic properties.

Thus, the present invention relates to a stable emulsion, of the water-in-oil or oil-in-water type, comprising a continuous phase and a dispersed phase in the form of drops, wherein the drops comprise a shell formed by at least one anionic polymer comprising at least one carboxylic acid function, and at least one cationic polymer comprising at least two amine functions, in which the quantity of amine functions provided by the cationic polymer in the phase under consideration is between 0.2 µmol and 10.5 µmol per gram of the phase.

According to one embodiment, the present invention relates to an oil-in-water type emulsion, comprising an aqueous continuous phase and a dispersed fatty phase in the form of drops, wherein the drops comprise a shell formed by at least one anionic polymer comprising at least one carboxylic acid function, and at least one cationic polymer comprising at least two amine functions, in which the quantity of amine functions provided by the cationic polymer in the fatty phase is between 0.2 µmol and 10.5 µmol per gram of fatty phase.

According to another embodiment, the present invention relates to a water-in-oil emulsion, comprising a continuous fatty phase and an aqueous dispersed phase in the form of drops, wherein the drops comprise a shell formed by at least one anionic polymer comprising at least one carboxylic acid function, and at least one cationic polymer comprising at least two amine functions, in which the quantity of amine functions provided by the cationic polymer in the fatty phase is between 0.2 µmol and 10.5 µmol per gram of fatty phase.

According to one embodiment, the quantity of amine functions provided by the cationic polymer in the fatty phase, is between 0.3 µmol and 7 µmol, preferably between 0.4 µmol and 5 µmol, in particular between 0.8. µmol and 3 µmol, and better still between 0.8 µmol and 2 µmol, per gram of fatty phase.

In the context of the invention, and unless otherwise stated, the term "amine function" is understood to mean an —$NH_2$ function.

In fact, in the context of a coacervate-stabilized emulsion resulting from the interaction between an anionic polymer, in particular a carbomer, and a cationic polymer, in particular an amodimethicone, the inventors observed that the density of amine functions provided by the cationic polymer in the fatty phase impacts the properties of the drops forming the emulsion in terms of mechanical strength, including shear strength or fragmentation, and resistance to coalescence.

In the context of the invention, and unless otherwise indicated, the term "quantity of amine functions in the fatty phase" is understood to mean the total quantity of amine functions (or groups or groupings) present in the fatty phase. It may, for example, relate to amine functions provided by the cationic polymer or by any other compound present in the fatty phase. In fact, the fatty phase may comprise, in addition to the cationic polymer, compounds that are different from the cationic polymer and which comprise at least one amine function, such as for example N-acetylglucosamine.

In the context of the invention, and unless otherwise stated, the term "quantity of amine functions provided by the cationic polymer, in the fatty phase" is understood to mean the quantity of amine functions (or groups or groupings) present in the fatty phase, which are only carried by (or present on) the cationic polymer. Thus, the quantity of amine functions provided by the cationic polymer in the fatty phase does not include the quantity of amine functions carried by any other compound other than the cationic polymer in this fatty phase.

For obvious reasons, the amine functions provided by the cationic polymer in question are those capable of reacting with the anionic polymer, in particular with the carboxylic groups carried by the anionic polymer.

Thus, advantageously, at least 50%, preferably at least 60%, in particular at least 70%, better still at least 80%, more preferably at least 90%, and most preferably at least 99%, of the amine functions provided by (or present on) the cationic polymer are capable of reacting with the anionic polymer, in particular with the carboxylic groups carried by the anionic polymer.

The dispersions according to the invention are advantageously stable at ambient or elevated temperature (for example up to 50° C.). They also have little or no coalescence. Thus, the drops of the dispersion may retain their attractive aesthetic appearance sought by the consumer. This interesting property in terms of kinetic stability is all the more unexpected as the shell of the drops as described in detail below, is very fine. Thus, at the time of application to a keratin material, no resistance attached to the breaking of the shell is felt by the user and no residual deposit of the shell is otherwise noted. This is referred to as an evanescent shell.

The drops of a dispersion according to the invention, by the nature and the properties of their shells, therefore, differ from solid capsules, i.e. capsules provided with a solid membrane, such as, for example, those described in WO 2010/063937.

In addition, the dispersions according to the invention advantageously have high mechanical strength, which makes it possible to avoid shearing or fragmentation of the drops, especially during their industrialization or transport.

In the context of the present invention, the above-mentioned emulsions may be denoted by the term "dispersions".

According to the invention, the pH of an emulsion is typically between 5.5 and 7.0.

A drop according to the invention is composed of a heart, also called the interior of the drop, surrounded by a shell, which isolates the inside of the drop from the continuous phase of the emulsion.

According to one embodiment, the emulsions according to the invention do not comprise a surfactant. They are therefore different in this case from the usual emulsions/cosmetic compositions.

According to one embodiment, an emulsion according to the invention is prepared by implementing a "non-microfluidic" method, i.e. by simple emulsification. According to this embodiment, the drop size of the dispersed phase is less than 500 µm, or even less than 200 µm. Preferably, the size of the drops is between 0.5 µm and 50 µm, preferably between 1 µm and 20 µm.

According to this embodiment, the present invention makes it possible to have drops of reduced size, especially with respect to drops obtained by a microfluidic method. This small size of drops will have an effect on the texture. In fact, an emulsion according to the invention, formed of finely dispersed drops, offers improved lubricity qualities.

According to another embodiment, an emulsion according to the invention is prepared by implementing a "microfluidic" method, in particular as described below. According to this embodiment, the drop size of the dispersed phase is greater than 500 µm, or even greater than 1000 µm. Preferably, according to this embodiment, the size of the drops is between 500 µm and 3000 µm, preferably between 1000 µm and 2000 µm. As such, it was not obvious that the compositions comprising such drops of size greater than 500 µm, would be stable.

In the context of the present invention, the term "size" is understood to mean the diameter, in particular the average diameter of the drops.

According to one embodiment, an emulsion according to the invention is of the oil-in-water type.

According to another embodiment, an emulsion according to the invention is of the water-in-oil type.

Viscosity

The viscosity of the emulsions according to the invention may vary significantly, which thus makes it possible to obtain varied textures.

According to one embodiment, the emulsion according to the invention has a viscocisty of from 1 mPa·s to 500,000 mPa·s, preferably from 10 mPa·s to 300,000 mPa·s, and even more preferably from 1,000 mPa·s to 100,000 mPa·s as measured at 25° C.

The viscosity is measured at ambient temperature, for example T=25° C.±2° C., and at ambient pressure, for example 1013 mbar, by the method described below.

A Brookfield type viscometer, typically a Brookfield RVDV-E digital viscometer (spring twist torque of 7187.0 dyne-cm), i.e. a rotational speed viscometer equipped with a spindle, is used. A rotational speed is imposed on the spindle and the measurement of the torque exerted on the spindle makes it possible to determine the viscosity by knowing the geometry/shape parameters of the spindle used.

For example, a spindle of size No. 04 (Brookfield reference: RV4) is used. The shear rate corresponding to the measurement of the viscosity is defined by the spindle used and the speed of rotation thereof.

The viscosity measurement is carried out for 1 minute at room temperature (T=25° C.±2° C.). About 150 g of solution are placed in a beaker of 250 ml volume, having a diameter of about 7 cm so that the height of the volume occupied by the 150 g of solution is sufficient to reach the level marked on the spindle. Then, the viscometer is started at a speed of 10 rpm until the value displayed on the screen becomes stable. This measurement gives the viscosity of the tested fluid, as mentioned in the context of the present invention.

Fatty Phase

According to one embodiment, the emulsions according to the invention comprise a fatty phase, in particular dispersed in the form of drops.

The fatty phase of an emulsion according to the invention may comprise at least one oil and/or at least one fatty substance that is solid at ambient temperature and pressure, in particular as defined below.

Oil(s)

According to one embodiment, the drops of the dispersed phase may comprise at least one oil. The dispersed fatty phase may therefore be designated as an oily phase.

According to one embodiment, the fatty phase comprises an oil H1 in which the cationic polymer is soluble. In particular, the emulsion according to the invention comprises at least one oil compatible with the cationic polymer. The oil H1 corresponds, for example, to a good solvent of the cationic polymer.

The emulsions according to the invention may comprise a single oil H1 or a mixture of several oils H1. An emulsion according to the invention may therefore comprise at least one, at least two, at least three, at least four, at least five or more oils H1, such as those described below.

The term "oil" is understood to mean a fatty substance that is liquid at room temperature (25° C.).

As oils H1 used in the emulsion of the invention may be mentioned, for example:

hydrocarbon oils of animal origin, such as perhydrosqualene and squalane;

esters and synthetic ethers, in particular of fatty acids, such as the oils of formulas $R_1COOR_2$ and $R_1OR_2$ in which $R_1$ represents the residue of a $C_8$ to $C_{29}$ fatty acid, while $R_2$ represents a hydrocarbon chain, branched or unbranched, $C_3$ to $C_{30}$, such as, for example, an oil sold under the trademark Purcellin Oil® (cetearyl ethylhexanoate), isononyl isononanoate, isodecyl neopentanoate, isopropyl myristate, 2-ethylhexyl palmitate, octyl-2 stearate dodecyl, octyl-2-dodecyl erucate, isostearyl isostearate; hydroxylated esters such as isostearyl lactate, octyl hydroxystearate, octyldodecyl hydroxystearate, diisostearyl malate, triisocetyl citrate, heptanoates, octanoates, demayoates of fatty alcohols; polyol esters, such as propylene glycol dioctanoate, neopentyl glycol diheptanoate and diethylene glycol diisononanoate; and pentaerythritol esters such as the product pentaerythrityl tetrahehenate sold under the trade name DUB PTB or the product pentaerythrityl tetraisostearate sold under the trademark Prisorine® 3631;

linear or branched hydrocarbons of mineral or synthetic origin, such as paraffin oils, volatile or not, and their derivatives, petroleum jelly, polydecenes, the product hydrogenated polyisobutene sold under the trademark Parleam® oil;

silicone oils, for example volatile or non-volatile polymethylsiloxanes (PDMS) with a linear or cyclic silicone chain, which are liquid or pasty at room temperature, in particular cyclopolydimethylsiloxanes (cyclomethicones) such as cyclohexasiloxane and cyclopentasiloxane; polydimethylsiloxanes (or dimethicones) comprising alkyl, alkoxy or phenyl groups, during or at the end of the silicone chain, groups having from 2 to 24 carbon atoms; phenyl silicones such as phenyltrimethicones, phenyldimethicones, phenyltrimethylsiloxydiphenylsiloxanes, diphenyldimethi-cones, diphenylmethyldiphenyltrisiloxanes, 2-phenylethyltrimethylsiloxysilicates, and polymethylphenylsiloxanes;

fatty alcohols having from 8 to 26 carbon atoms, such as cetyl alcohol, stearyl alcohol and their mixture (cetylstearyl alcohol), or else octyldodemayol; partially fluorinated hydrocarbon oils and/or silicone oils such as those described in document JP-A-2-295912; and their mixtures.

According to one embodiment, the oil H1 is chosen from the esters of formula $R_1COOR_2$, in which $R_1$ represents the residue of a $C_8$ to $C_{29}$ fatty acid, while $R_2$ represents a hydrocarbon chain, branched or unbranched, in $C_3$ to $C_{30}$.

According to one embodiment, the oil H1 is chosen from fatty alcohols having from 8 to 26 carbon atoms.

According to one embodiment, the oil H1 is chosen from hydrocarbon oils having from 8 to 16 carbon atoms, and in particular $C_8$-$C_{16}$ branched alkanes (also known as isoparaffins or isoalkanes), such as isododemaye (also called 2,2,4,4,6-pentamethylheptane), isodemaye, isohexademaye, and, for example, oils sold under the trade names Isopars® or Permethyls®.

According to a preferred embodiment, the oil H1 is chosen from the group consisting of isononyl isononanoate, dimethicone, isohexademaye, polydimethylsiloxane, octyldodemayol, isodecyl neopentanoate and their mixtures.

Preferably, the oil H1 is isononyl isononanoate.

According to one embodiment, the oil H1 is not a vegetable oil.

According to one embodiment, the oil H1 is not represented by polydimethylsiloxane (PDMS), and preferably is not a silicone oil.

According to another embodiment, the fatty phase of the drops does not comprise polydimethylsiloxane (PDMS), and preferably does not include silicone oil.

According to a preferred embodiment, an emulsion according to the invention comprises at least 1% by weight of oil(s) H1, preferably isononyl isononanoate, relative to the total weight of the emulsion.

According to one embodiment, the content of oil(s) H1 in the fatty phase is between 1% and 99.99%, preferably between 20% and 90%, and in particular between 50% and 80%, by weight, relative to the total weight of the fatty phase.

According to one embodiment, the fatty phase of the emulsions of the invention may further comprise at least one hydrocarbon oil H2 of plant origin. The fatty phase may comprise several oils H2.

As vegetable oils H2, particular mention may be made of liquid triglycerides of $C_4$-$C_{10}$ fatty acids such as triglycerides of heptanoic or octanoic acids, or else, for example, sunflower, corn, soybean, squash, coconut and grapes, sesame, hazelnut, apricot, 10 macadamia, arara, sunflower, castor, avocado, caprylic/capric acid triglycerides, such as those marketed by the company Stéarineries Dubois or those available under the trademark "Miglyol® 810" (C6, C8, C10, C12 medium chain triglycerides), "Miglyol® 812" (and 55% triglycerides of C8 and 45% triglycerides of C10 fatty acids) "Miglyol® 818" (triglyceride of the fractionated C8 and C10 plant fatty acids, plus about 4 to 5% linoleic acid) by Dynamit Nobel, jojoba oil, or shea butter oil.

Among the oils H2, mention may also be made of the following compounds: $C_{10}$-$C_{18}$ triglycerides which are liquid at room temperature (25° C.), triglycerides of caprylic and capric acids (INCI name: Caprylic/Capric Triglyceride), triglycerides of caprylic, capric, myristic and stearic acids (INCI name: Caprylic/capric/myristic/stearic Triglyceride), triethylhexanoine, hydrogenated vegetable oil, meadowfoam seed oil *Limnanthes Alba* (INCI name: *Limnanthes Alba* (Meadowfoam Seed Oil), *Olea Europaea* olive oil (INCI name: *Olea Europaea* (Olive) Fruit Oil), *Macadamia* nut oil (INCI name: *Macadamia Ternifolia* Seed Oil), Rosehip rose oil Mayina (INCI name: *Rosa Mayina* Fruit Oil), soybean oil (INCI name: *Glycine Soja* (Soybean) Oil), sunflower seed oil (INCI name: *Helianthus Annuus* (Sunflower) Seed Oil), the corn oil (INCI name: *Zea Mays* (Corn) Oil), hydrogenated palm oil (INCI name: Hydrogenated Palm Oil), tribehenine (INCI name: tribehenin), triisostearin (INCI name: triisostearin), apricot kernel oil (INCI name: *Prunus Armeniaca* (Apricot) Kernel Oil), rice bran oil (INCI name: *Oryza Sativa* (Rice) Bran Oil), argan oil (INCI name: *Argania Spinosa* Kernel Oil), avocado oil (INCI name: *Persea Gratissima* Oil), evening primrose oil (INCI name: *Oenothera Biennis* Oil), palm oil (INCI name: *Elaeis Guineensis* Oil), rice germ oil (INCI name: *Oryza Sativa* Germ Oil), hydrogenated coconut (INCI name: Hydrogenated Coconut Oil), sweet almond oil (INCI name: *Prunus Amygdalus Dulcis* Oil), grape seed oil (INCI name: *Vitis Vinifera* Seed Oil), oil of sesame seed (INCI name: *Sesamum Indicum* Seed Oil), peanut seed oil (INCI name: *Arachis Hypogaea* Oil), hydrogenated rapeseed oil (INCI name: Hydrogenated Rapeseed Oil), oil of *Mortierella isabellina* (INCI name: *Mortierella* Oil), safflower seed oil (INCI name: *Carthamus Tinctorius* Seed Oil), Queensland nut oil *Macadamia integrifolia* (INCI name: *Macadamia Integrifolia* Seed Oil), tricaprylin (or triacylglycerol), vegetable oil (INCI name: Olus Oil), palm oil extracted from the nucleus (INCI name: *Elaeis Guineensis* Kernel Oil), coconut oil (INCI name: *Cocos Nucifera* Oil), wheat germ oil (INCI name: *Triticum Vulgare* Germ Oil), borage seed oil (INCI name: *Borago Officinalis* Seed Oil), shea oil (INCI name: *Butyrospermum Parkii* Oil), hazelnut oil (INCI name: *Corylus Avellana* Seed Oil), hydrogenated castor oil (INCI name: Hydrogenated Castor Oil), hydrogenated palm kernel oil (INCI name: Hydrogenated Palm Kernel Oil), oil of mango seed (INCI name: *Mangifera Indica* Seed Oil), pomegranate seed oil (INCI name: *Punica Granatum* Seed Oil), Chinese cabbage seed oil (INCI name: *Brassica Campestris* Seed Oil), passion fruit seed oil (INCI name: *Passiflora Edulis* Seed Oil), *camellia* seed oil of Japan (INCI name: *Camellia Japonica* Seed Oil), green tea seed oil (INCI name: *Camellia*

Sinensis Seed Oil), corn germ oil (INCI name: *Zea Mays* Germ Oil), oil of hoplostete (INCI name: Hoplostethus Oil), Brazil nut oil (INCI name: *Bertholletia Excelsa* Seed Oil), musk rose seed oil (INCI name: *Rosa Moschata* Seed Oil), *Inca* seed Inchi (or Sacha Inchi) (INCI name: *Plukenetia Volubilis* Seed Oil), Babassu seed oil (INCI name: Orbignya Oleifera Seed Oil), the seed oil of a hybrid sunflower strain (INCI name: *Helianthus Annuus* Hybrid Oil), sea buckthorn oil (INCI name: Hippophae Rhamnoides Oil), Marula seed oil (INCI name: *Sclerocarya Birrea* Seed Oil), *Aleurites Molucmaya* Seed Oil (INCI name: *Aleurites Molucmaya* Seed Oil), Ruby Seed Oil (INCI Name: *Rosa Rubiginosa* Seed Oil), *Camellia Kissi* Seed Oil (INCI name: *Camellia Kissi* Seed Oil), baobab seed oil (INCI name: *Adansonia Digitata* Seed Oil), baobab oil (INCI name: *Adansonia Digitata* Oil), *Moringa* seed oil (INCI name: *Moringa Pterygosperma* Seed Oil), *perilla* sheath oil (INCI name: *Perilla Ocymoides* Seed Oil), castor seed oil (INCI name: *Ricinus Communis* Seed Oil), mayola oil (INCI name: Mayola Oil), black currant seed oil (INCI name: *Ribes Nigrum* Seed Oil), tea seed oil (INCI name: *Camellia Oleifera* Seed Oil), raspberry seed oil (INCI name: *Rubus Idaeus* Seed Oil), Abyssinian *crambe* seed oil (INCI name: *Crambe Abyssinica* Seed Oil), rosehip seed oil (INCI name: *Rosa Mayina* Seed Oil), vine plantain oil (INCI name: *Echium Plantagineum* Seed Oil), tomato seed oil (INCI name: *Solanum Lycopersicum* Seed Oil), bitter almond oil (INCI name: *Prunus Amygdalus Amara* Kernel Oil), yuzu seed oil (INCI name: Citrus Junos Seed Oil), pumpkin seed oil (INCI name: *Cucurbita Pepo* Seed Oil), *Mustela* Mustelidae mink oil (INCI name: *Mustela* Oil), Desert Date Seed Oil (INCI name: *Balanites Roxburghii* Seed Oil), *Brassica Napus* Seed Oil (INCI name: *Brassica Napus* Seed Oil), *Calophyllum Inophyllum* (INCI Name: *Calophyllum Inophyllum*) Seed Oil), Arctic Mature Seed Oil (INCI name: *Rubus* Chamaemorus Seed Oil), Japanese White Pine Seed Oil (INCI name: *Pinus Pentaphylla* Seed Oil), Watermelon Seed Oil (INCI name: *Citrullus Lanatus* Seed Oil), walnut seed oil (INCI name: *Juglans Regia* Seed Oil), *nigella* (INCI name: *Nigella Sativa* Seed Oil), carrot seed oil (INCI name: *Daucus Carota Sativa* Seed Oil), *Coix Lacryma-jobi* Mayuen seed oil (INCI name: *Coix Lacryma-jobi* Ma-yen Seed Oil), *Coix Lacryma-jobi* seed oil (INCI name: *Coix Lachryma-Jobi* Seed Oil), the lipid blend of *Triticum Vulgare* flour (INCI name: *Triticum Vulgare* Flour Lipids), trihydroxymethoxystearin (INCI name: Trihydroxymethoxystearin), triheptanoine (INCI name: Triheptanoin), cranberry seed oil (INCI name: *Vaccinium Macrocarpon* Seed Oil), vanilla oil (INCI name: *Vanilla Planifolia* Fruit Oil), cranberry seed oil (INCI name: *Oxycoccus Palustris* Seed Oil), Acai oil (INCI name: *Euterpe Oleracea* Fruit Oil), triester of hydrogenated castor oil and isostearic acice (INCI name: Hydrogenated Castor Oil Triisostearate), hydrogenated cottonseed oil (INCI name: Hydrogenated Cottonseed Oil) Hygrogenated olive oil (INCI name: Hydrogenated Olive Oil), hydrogenated peanut oil (INCI name: Hydrogenated Peanut Oil), hydrogenated soybean oil (INCI name: Hydrogenated Soybean Oil), oil extracted from chicken egg yolk (INCI name: Egg Yolk Oil), peach kernel core oil (INCI name: *Prunus Persica* Kernel Oil), glycerides from mayola oil and phytosterols (INCI name: Phytosteryl Mayola Glycerides), black currant seed oil (INCI name: *Ribes Nigrum* (Black Currant) Seed Oil), karanja seed oil (INCI name: *Pongamia Glabra* Seed Oil) and roucou oil (INCI name: Roucou (*Bixa orellana*) Oil), olive oil extract, especially phytosqualane, rosehip oil, coriander oil, linseed oil, chia oil, Fenugreek oil, hemp oil, and mixtures thereof.

Preferably, the oil H2 is chosen from oils rich in polyunsaturated fatty acids.

For the purposes of the present invention, the term "unsaturated fatty acid" is understood to mean a fatty acid comprising at least one double bond. It is more particularly a long chain fatty acid, i.e. that may have more than 14 carbon atoms. The unsaturated fatty acids may be in acid form, or in salt form, for example their calcium salt, or in the form of derivatives, in particular of fatty acid ester(s).

Preferably, the oil H2 is chosen from oils rich in long-chain fatty acids, i.e. that are able to have more than 14 carbon atoms, and better unsaturated fatty acids containing from 18 to 22 carbon atoms. especially ω-3 and ω-6 fatty acids. Thus, advantageously, the vegetable oils are chosen from evening primrose, borage, blackcurrant seed, hemp, walnut, soybean, sunflower, wheat germ, fenugreek, rosebush and musk rosebush oils. echium, argan, baobab, rice bran, sesame, almond, hazelnut, chia, flax, olive, avocado, safflower, coriander, rapeseed (in particular *Brassica naptus*), and their mixtures.

Preferably, the oil H2 is chosen from matt and non-glossy oils. In particular, mention may be made of *Moringa* oil.

According to one embodiment, the content of oil(s) H2 in the fatty phase is between 0% and 40%, preferably between 0.1% and 25%, and in particular between 1% and 20%, by weight. relative to the total weight of the fatty phase.

According to one embodiment, the mass ratio between the quantity of oil(s) H1 and the quantity of oil(s) H2 ranges from 0.025 to 99.99, preferably from 0.8 to 90, and in particular from 2.5 to 80.

The fatty phase may further comprise at least one other oil different from the oils H1 and H2.

An emulsion according to the invention of the oil-in-water type may comprise from 0.0001% to 50%, preferably from 0.1% to 40%, and better still from 1% to 25%, by weight of oil(s) relative to the total weight of the emulsion.

An emulsion according to the invention of the water-in-oil type may comprise from 50% to 89.9%, preferably from 55% to 80%, and better still from 60% to 70%, by weight of oil(s) relative to the total weight of the emulsion.

Solid Fatty Substances

According to one embodiment, the drops of the dispersed phase may comprise at least one solid fatty substance at room temperature and pressure, selected from waxes, pasty fatty substances, butters, and mixtures thereof.

Wax(es)

For the purposes of the invention, the term "wax" is understood to mean a lipophilic compound that is solid at room temperature (25° C.), with a reversible solid/liquid state change, having a melting point greater than or equal to 30° C. up to 120° C.

The protocol for measuring this melting point is described below.

The waxes that may be used in an emulsion according to the invention may be chosen from waxes, solid, deformable or not, at room temperature, of animal, vegetable, mineral or synthetic origin, and mixtures thereof.

In particular, it is possible to use hydrocarbon-based waxes such as beeswax, lanolin wax, and Chinese insect waxes; rice wax, Carnauba wax, Maydelilla wax, Ouricurry wax, Alfa wax, cork fiber wax, sugar maye wax, Japanese wax and sumac wax; montan wax, microcrystalline waxes, paraffins and ozokerite; polyethylene waxes, waxes obtained by Fisher-Tropsch synthesis and waxy copolymers and their esters, and mixtures thereof.

Mention may also be made of waxes obtained by catalytic hydrogenation of animal or vegetable oils having linear or branched $C_8$-$C_{32}$ fatty chains.

Among these may be mentioned hydrogenated jojoba oil, hydrogenated sunflower oil, hydrogenated castor oil, hydrogenated coconut oil and hydrogenated lanolin oil, the product ditetrastearate (trimethylo1-1,1,1 propane) sold under the product name "HEST 2T-4S" by the company HETERENE, the product di-(1,1,1-trimethylolpropane) tetraprenate sold under the product name HEST 2T-4B by the company HETERENE.

It is also possible to use the waxes obtained by transesterifica-tion and hydrogenation of vegetable oils, such as castor oil or olive oil, such as the waxes sold under the tradmarks Phytowax® ricin 16L64® and 22L73® and Phytowax® Olive 18L57 by the company Sophim. Such waxes are described in application FR-A-2792190.

It is also possible to use silicone waxes, which may advantageously be 15 polysiloxanes, preferably substituted at a low melting point.

Among the commercial silicone waxes of this type, mention may be made in particular of those sold under the trademarks Abil® wax 9800, 9801 or 9810 (GOLDSCHMIDT), KF910 and KF7002 (SHIN ETSU), or 176-1118-3 and 176-11481 (GENERAL ELECTRIC).

The silicone waxes that may be used may also be alkyl or alkoxydimethicones such 20 as the following commercial products: under the trademark Abil® wax 2428, 2434 and 2440 (GOLDSCHMIDT), or VP 1622 and VP 1621 (WACKER), as well as (C20-C60) alkyldimethicones, in particular especially the (C30-C45) alkyldimethicones such as the silicone wax sold under the name SF-1642 by the company GE-Bayer Silicones.

It is also possible to use hydrocarbon waxes modified with silicone or fluorinated groups such as, for example, siliconyl maydelilla, siliconyl beeswax and Fluorobeeswax by Koster Keunen.

The waxes may also be chosen from fluorinated waxes.

Butter(s) or Pasty Fatty Substances

For the purposes of the present invention, the term "butter" (also referred to as "pasty fatty substance") is understood to mean a lipophilic fatty compound with a reversible solid/liquid state change and comprising a liquid fraction and a solid fraction at the temperature of 25° C. and at atmospheric pressure (760 mmHg). In other words, the starting melting temperature of the pasty compound may be less than 25° C. The liquid fraction of the pasty compound measured at 25° C. may represent from 9% to 97% by weight of the compound. This liquid fraction at 25° C. is preferably between 15% and 85%, more preferably between 40% and 85% by weight. Preferably, the one or more butters have an end-of-melting temperature of less than 60° C. Preferably, the butter or butters have a hardness less than or equal to 6 MPa.

Preferably, the butters or pasty fatty substances have an anisotropic crystalline organization in the solid state that is visible by X-ray observations. For the purposes of the invention, the melting temperature corresponds to the temperature of the most endothermic peak observed in thermal analysis (DSC) as described in ISO 11357-3; 1999. The melting point of a paste or a wax may be measured using a differential scanning calorimeter (DSC), for example the calorimeter sold under the name "DSC Q2000" by the company TA Instruments.

Concerning the measurement of the melting temperature and the determination of the end-of-melting temperature, the sample preparation and measurement protocols are as follows: A sample of 5 mg of pasty fatty substance (or butter) or wax previously heated to 80° C. and taken with magnetic stirring using an equally-heated spatula is placed in an airtight aluminum capsule or crucible. Two tests are carried out to ensure the reproducibility of the results.

The measurements are made on the calorimeter mentioned above. The oven is subjected to a nitrogen sweep. The cooling is ensured by the RCS heat exchanger 90. The sample is then subjected to the following protocol, first being brought to a temperature of 20° C. and then subjected to a first temperature rise ranging from 20° C. to 80° C. at the heating rate of 5° C./minute, then cooled from 80° C. to −80° C. at a cooling rate of 5° C./minute, and finally subjected to a second temperature rise from −80° C. to 80° C. at a heating rate of 5° C./minute. During the second temperature rise, the variation of the power difference absorbed by the empty crucible and the crucible containing the butter sample is measured as a function of the temperature. The melting point of the compound is the value of the temperature corresponding to the peak apex of the curve representing the variation of the difference in power absorbed as a function of the temperature. The end-of-melting temperature corresponds to the temperature at which 95% of the sample is melted.

The liquid fraction by weight of the butter (or pasty fatty substance) at 25° C. is equal to the ratio of the enthalpy of fusion absorbed at 25° C. and the enthalpy of the melting of the butter. The enthalpy of the melting of the butter or pasty compound is the enthalpy consumed by the compound to pass from the solid state to the liquid state.

The butter is said to be in the solid state when the entirety of its mass is in crystalline solid form. The butter is said to be in the liquid state when the entirety of its mass is in liquid form. The melting enthalpy of the butter is equal to the integral of the whole of the melting curve obtained with the aid of the proposed calorimeter, with a rise in temperature of 5° C. or 10° C. per minute, according to the standard ISO 11357-3: 1999. The melting enthalpy of the butter is the quantity of energy required for the compound to pass from the solid state to the liquid state. It is expressed in J/g.

The enthalpy of fusion consumed at 25° C. is the quantity of energy absorbed by the sample to change from the solid state to the state it exhibits at 25° C. consisting of a liquid fraction and a solid fraction. The liquid fraction of the butter measured at 32° C. preferably represents from 30% to 100% by weight of the compound, preferably from 50% to 100%, more preferably from 60% to 100% by weight of the compound. When the liquid fraction of the butter measured at 32° C. is 100%, the temperature of the end of the melting range of the pasty compound is less than or equal to 32° C. The liquid fraction of the butter measured at 32° C. is equal to the ratio of the melting enthalpy absorbed at 32° C. and the enthalpy of the melting of the butter. The melting enthalpy absorbed at 32° C. is calculated in the same way as the melting enthalpy absorbed at 23° C.

As regards the measurement of the hardness, the sample preparation and measurement protocols are as follows: the composition according to the invention or the butter is placed in a mold 75 mm in diameter which is filled to about 75% of its height. In order to overcome the thermal past and control the crystallization, the mold is placed in the Vötsch VC0018 programmable oven, where it is first heated to 80° C. for 60 minutes, then cooled from 80° C. to 0° C. at a cooling rate of 5° C./minute, then left at the stabilized temperature of 0° C. for 60 minutes, then subjected to a temperature rise from 0° C. to 20° C. at a rate of 5° C./minute, then left at the stabilized temperature of 20° C.

for 180 minutes. The compressive force measurement is performed with Swantech's TA/TX2i texturometer. The spindle used is chosen according to the texture: a cylindrical steel spindle of 2 mm diameter for very rigid raw materials; a cylindrical steel spindle of 12 mm diameter for rigid raw materials. The measurement comprises 3 steps: a first step after automatic detection of the surface of the sample where the spindle moves at the measurement speed of 0.1 mm/s, and enters the composition according to the invention or the butter to a penetration depth of 0.3 mm, wherein the software records the value of the maximum force reached; a second so-called relaxation step where the spindle stays at this position for one second and where the force is noted after 1 second of relaxation; finally a third so-called withdrawal step where the spindle returns to its initial position at a speed of 1 mm/s and the energy of withdrawal of the probe (negative force) is noted.

The value of the hardness measured in the first step corresponds to the maximum compressive force measured in Newton divided by the surface area of the texturometer cylinder expressed in $mm^2$ in contact with the butter or the composition according to the invention. The value of hardness obtained is expressed in mega-pascals or MPa.

The pasty fatty substance or butter may be chosen from synthetic compounds and compounds of plant origin. A pasty fatty substance may be obtained synthetically from starting materials of plant origin.

The pasty fatty substance is advantageously chosen from:
lanolin and its derivatives such as lanolin alcohol, oxyethylenated lanolines, acetylated lanolin, lanolin esters such as isopropyl lanolate, oxypropylenated lanolines,
polymeric or non-polymeric silicone compounds, such as polydimethylsiloxanes of high molecular weight, polydimethylsiloxanes with side chains of the alkyl or alkoxy type having from 8 to 24 carbon atoms, especially stearyl dimethicones,
polymeric or non-polymeric fluorinated compounds,
vinyl polymers, in particular
homopolymers of olefins,
olefin copolymers,
homopolymers and copolymers of hydrogenated dienes,
linear or branched oligomers, homo or copolymers of alkyl (meth) acrylates preferably having a $C_8$-$C_{30}$ alkyl group,
homo and copolymeric oligomers of vinyl esters having $C_8$-$C_{30}$ alkyl groups,
homo and copolymer oligomers of vinyl ethers having $C_8$-$C_{30}$ alkyl groups,
the liposoluble polyethers resulting from the poly-etherification between one or more $C_2$-$C_{100}$ and preferably $C_2$-$C_{50}$ diols,
esters and polyesters, and
their mixtures.

According to a preferred embodiment of the invention, the particular butter(s) is/are of plant origin, such as those described in Ullmann's Encyclopedia of Industrial Chemistry ("Fats and Fatty Oils", A. Thomas, published on 15 Jun. 2000, D01: 10.1002/14356007.a10_173, item 13.2.2.2 Shea Butter, Borneo Tallow, and Related Fats (Vegetable Butters).

More particularly, mention may be made of triglycerides $C_{10}$-$C_{18}$ (INCI name: $C_{10}$-$C_{18}$ Triglycerides) comprising a liquid fraction and a solid fraction at a temperature of 25° C. and at atmospheric pressure (760 mm Hg), shea butter, Nilotica Shea butter (*Butyrospermum parkii*), Galam butter, (*Butyrospermum parkii*), Borneo butter or fat or Tengkawang tallow) (Shorea stenoptera), Shorea butter, Illipé butter, *Madhuca* butter or *Bassia Madhuca longifolia*, mowrah butter (*Madhuca Latifolia*), Katiau butter (*Madhuca mottleyana*), Phulwara butter (*M. butyracea*), mango butter (*Mangifera indica*), Murumuru butter (*Astrocatyum murumuru*), Kokum butter (*Garcinia Indica*), Ucuuba butter (*Virola sebifera*), Tucuma butter, Painya butter (Kpangnan) (*Pentadesma butyracea*), Coffee butter (*Coffea arabica*), Apricot butter (*Prunus Armeniaca*), Macadamia butter (*Macadamia Temifolia*), butter butter grape (*Vitis vinifera*), avocado butter (*Persea gratissima*), olive butter (*Olea europaea*), sweet almond butter (*Prunus amygdalus dulcis*), cocoa butter (*Theobroma cacao*) and sunflower butter, butter under the INCI name *Astrocaryum Murumuru* Seed Butter, butter under the INCI name *Theobroma Grandiflorum* Seed Butter, and butter under the INCI name *Irvingia Gabonensis* Kernel Butter, jojoba esters (mixture of wax and oil hydrogenated jojoba) (INCI name: Jojoba esters) and ethyl esters of shea butter (INCI name: Shea butter ethyl esters), and mixtures thereof.

Of course, those skilled in the art will take care to choose the solid fat(s) and/or their quantity in such a way that the advantageous properties of the emulsion according to the invention are not, or not substantially, impaired by the envisaged addition, in particular to preserve the integrity of the emulsion according to the invention and in particular of the shell (or membrane) of the dispersed drops. These adjustments are within the competence of persons skilled in the art.

Preferably, an emulsion according to the invention may comprise from 0% to 98.99% by weight, preferably from 0.5% to 70% by weight, in particular from 1% to 30% by weight, and better still from 1% to 20% by weight, of solid fatty substance(s) relative to the total weight of the fatty phase.

According to one embodiment, the fatty phase has a viscosity of from 0.1 mPa·s to 1,000,000 mPa·s, preferably from 0.5 mPa·s to 500,000 mPa·s, and better still from 1 mPa·s to 1,000 mPa·s as measured at 25° C. The measurement of the viscosity is typically carried out according to the method detailed above for the measurement of the viscosity of the emulsion.

Shell of the Drops

As mentioned above, the drops of an emulsion according to the invention are surrounded by a shell (also referred to as a "membrane").

According to the invention, the drops obtained may have a very thin shell, in particular with a thickness less than 1% of the diameter of the drops.

The thickness of the shell is thus preferably less than 1 μm and is too small to be measured by optical methods.

According to one embodiment, the thickness of the shell of the drops is less than 1000 nm, especially between 1 nm and 500 nm, preferably less than 100 nm, advantageously less than 50 nm, and more preferably less than 10 nm.

The measurement of the thickness of the shell of the drops of the invention may be carried out by the Small-Angle X-ray Scattering method, as implemented in Sato et al. J. Chem. Phys. 111, 1393-1401 (2007), herein incorporated by reference.

For this purpose, the drops are produced using deuterated water and are then washed three times with a deuterated oil, such as, for example, a deuterated hydrocarbon-type oil (octane, dodemaye, hexademaye).

After washing, the drops are then transferred to the Neutrons cell to determine the I(q) spectrum; wherein q is the wave vector.

From this spectrum, conventional analytical treatments (REF) are applied to determine the thickness of the hydrogenated (undeuterated) shell.

According to one embodiment, the shell surrounding the drops of the dispersed phase is stiffened, which, in particular, gives good resistance to drops and reduces, or even prevents, their coalescence.

This shell is typically formed by coacervation, i.e. precipitation of charged polymers of opposite charges. Within a coacervate, the bonds binding the charged polymers to each other are of the ionic type, and are generally stronger than bonds present within a membrane of the surfactant type.

The shell is formed by coacervation of at least two charged polymers of opposite polarity (or polyelectrolyte) and preferably in the presence of a first polymer of the cationic type, and a second polymer, different from the first polymer, of the anionic type. These two polymers act as stiffening agents for the membrane.

The formation of the coacervate between these two polymers is generally caused by a modification of the conditions of the reaction medium (temperature, pH, reagent concentration, etc.). The coacervation reaction results from the neutralization of these two charged polymers of opposite polarities and allows the formation of a membrane structure by electrostatic interactions between the anionic polymer and the cationic polymer. The membrane thus formed around each drop typically forms a shell which completely encapsulates the heart of the drop and thus isolates the heart of the drop of the continuous phase.

Anionic Polymer

The aqueous phase, in particular the continuous aqueous phase, comprises at least one anionic polymer.

In the context of the present description, the term "anionic polymer" (or "anionic type polymer") is understood to mean a polymer having chemical functions of the anionic type. We may also speak of anionic polyelectrolyte.

The term "anionic chemical function" is understood to mean a chemical function AH capable of giving a proton to give a function $A^-$. According to the conditions of the medium in which it is found, the anionic type polymer therefore has chemical functions in AH form, or in the form of its conjugate base $A^-$.

As an example of chemical functions of the anionic type, mention may be made of the carboxylic acid functions —COOH, that are optionally present in the form of carboxylate anion —COO—.

As an example of an anionic type polymer, mention may be made of any polymer formed by the polymerization of monomers at least a part of which carries anionic type chemical functions, such as carboxylic acid functions. Such monomers are, for example, acrylic acid, maleic acid, or any ethylenically unsaturated monomer containing at least one carboxylic acid function. It may for example be an anionic polymer comprising monomeric units comprising at least one chemical function of carboxylic acid type.

Preferably, the anionic polymer is hydrophilic, i.e. soluble or dispersible in water. In the context of the invention, and unless otherwise indicated, the term "hydrophilic" is understood to mean the property according to which a given body is compatible with water or a polar solvent, i.e. it may accept water or the solvent, to form with them a homogeneous phase, for example a solution.

Examples of anionic polymer suitable for carrying out the invention include copolymers of acrylic acid or maleic acid and other monomers, such as acrylamide, alkyl acrylates, $C_5$-$C_8$ alkyl acrylates, $C_{10}$-$C_{30}$ alkyl acrylates, $C_{12}$-$C_{22}$ alkyl methacrylates, methoxypoly-ethylene glycol methacrylates, hydroxyester acrylates, crosspolymer acrylates.

According to one embodiment, the anionic polymer according to the invention is a carbomer or a crosslinked copolymer acrylates/$C_{10-30}$ alkyl acrylate. Preferably, the anionic polymer according to the invention is a carbomer.

According to one embodiment, the shell of the drops comprises at least one anionic polymer, such as for example a carbomer.

In the context of the invention, and unless otherwise indicated, the term "carbomer" is understood to mean an optionally crosslinked homopolymer resulting from the polymerization of acrylic acid. It is therefore an optionally crosslinked apoly(acrylic acid).

Among the carbomers of the invention, mention may be made of those sold under the trademark Tego®Carbomer 340FD from Evonik, the trademark Carbopol® 981 from Lubrizol, the trademark Carbopol® ETD 2050 from Lubrizol or the trademark Carbopol® Ultrez 10 from Lubrizol.

According to one embodiment, the term "carbomer" or "carbomer" or the trademark "Carbopol®" is understood to mean a high molecular weight acrylic acid polymer crosslinked with allyl sucrose or pentaerythritol allyl ethers (handbook of Pharmaceutical Excipients, 5th Edition, p111). Examples include the products sold under the trademarks Carbopol®910, Carbopol®934, Carbopol®934P, Carbopol®940, Carbopol®941, Carbopol®71G, Carbopol®980, Carbopol®971P or Carbopol®974P. According to one embodiment, the viscosity of the carbomer is between 4,000 cP and 60,000 cP at 0.5% w/w.

The carbomers have other names: polyacrylic acids, carboxyvinyl polymers or carboxy polyethylenes.

An emulsion according to the invention may comprise from 0.01% to 5%, preferably from 0.05% to 2%, and more preferably from 0.10% to 0.5%, by weight of anionic polymer(s), especially carbomer(s), relative to the total weight of the emulsion.

According to the invention, the anionic polymer may also be a crosslinked copolymer acrylates/$C_{10-30}$ alkyl acrylate (INCI name: acrylates/$C_{10-30}$ alkyl acrylate crosspolymer) as defined above.

According to the invention, the emulsions according to the invention may comprise a carbomer and a crosslinked acrylates/$C_{10-30}$ alkyl acrylate copolymer.

The aqueous phase according to the invention may also comprise at least one crosslinked polymer or at least one crosslinked copolymer, wherein the crosslinked polymer or crosslinked copolymer comprises at least one unit derived from the polymerization of one of the following monomers: acrylic or methacrylic acid, acrylate or alkyl methacrylate comprising from 1 to 30 carbon atoms, or their salts.

The aqueous phase may also comprise a mixture of crosslinked polymers or a mixture of crosslinked copolymers or a mixture of crosslinked polymer(s) and crosslinked copolymer(s).

According to the invention, the term "unit derived from the polymerization of a monomer" is understood to mean that the polymer or copolymer is a polymer or copolymer obtained by polymerization of the monomer.

According to one embodiment, the crosslinked polymer or the crosslinked copolymer is a crosslinked polyacrylate.

The crosslinked copolymers and polymers of the invention are anionic.

According to one embodiment, the copolymer is an unsaturated carboxylic acid copolymer and unsaturated $C_{1-30}$, preferably $C_{1-4}$, alkyl carboxylate. Such a copolymer comprises at least one hydrophilic unit of the olefinic unsaturated carboxylic acid type and at least one hydrophobic unit of the ($C_1$-$C_{30}$) alkyl ester type of unsaturated carboxylic acid.

Preferably, these copolymers are chosen from those whose hydrophilic unit of unsaturated olefinic carboxylic acid type corresponds to the following monomer of formula (I):

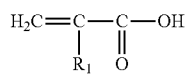

in which: $R_1$ denotes H or $CH_3$ or $C_2H_5$, i.e. units of acrylic acid, methacrylic acid or ethacrylic acid, and in which the hydrophobic unit of the ($C_1$-$C_{30}$) alkyl ester of unsaturated carboxylic acid type corresponds to the following monomer of formula (II):

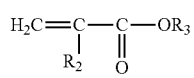

in which: $R_2$ denotes H or $CH_3$ or $C_2H_5$, (i.e. units of acrylate, methacrylate or ethacrylate units) and preferably H (acrylate units) or $CH_3$ (methacrylate units), $R_3$ denotes a $C_1$-$C_{30}$ alkyl radical; and preferably $C_1$-$C_4$.

Among this type of copolymer, those formed from a monomer mixture comprise:
(i) essentially acrylic acid,
(ii) an ester of formula (II) described above, and in which $R_2$ denotes H or $CH_3$, wherein $R_3$ denotes an alkyl radical having from 1 to 4 carbon atoms,
(iii) and a crosslinking agent, which is a well-known copolymerizable polyethylenic unsaturated monomer, such as diallyl phthalate, trimethylolpropane tri(meth)acrylate, diallyl itaconate, diallyl fumarate, diallyl maleate, zinc (meth) acrylate, (meth) allyl acrylate, divinylbenzene, (poly) ethylene glycol dimethacrylate, methylenebisacrylamide, and castor oil.

According to one embodiment, the crosslinked polymer or the crosslinked copolymer is a polymer or copolymer of acrylic acid and/or methacrylic acid, and/or of alkyl acrylate comprising from 1 to 30 carbon atoms, preferably of 1 to 4 carbon atoms, and/or alkyl methacrylate comprising 1 to 30 carbon atoms, preferably 1 to 4 carbon atoms.

According to one embodiment, the crosslinked copolymer is a crosslinked copolymer of methacrylic acid and of alkyl acrylate comprising from 1 to 4 carbon atoms, preferably 2 carbon atoms.

In the context of the invention, and unless otherwise stated, the term "crosslinked copolymer of methacrylic acid and of alkyl acrylate comprising from 1 to 4 carbon atoms" is understood to mean a crosslinked copolymer resulting from the polymerization of a monomer of methacrylic acid and an alkyl acrylate monomer comprising from 1 to 4 carbon atoms.

Preferably, in this copolymer, the methacrylic acid is from 20% to 80% by weight, preferably from 35% to 65% by weight of the total weight of the copolymer.

Preferably, in this copolymer, the alkyl acrylate is from 15% to 80% by weight, preferably from 35% to 65% by weight of the total weight of the copolymer.

In particular, the alkyl acrylate is chosen from alkyl methacrylate, ethyl acrylate and butyl acrylate.

According to one embodiment, the crosslinked polymer or the crosslinked copolymer according to the invention, present in the aqueous phase, is chosen from the group consisting of the following polymers or copolymers: Acrylates Copolymer, Acrylates crosspolymer-4, Acrylates crosspolymer-3, Polyacrylate-2 Crosspolymer and Polyacrylate-14 (INCI names).

Among the above polymers, according to the present invention, the products sold by LUBRIZOL under the trademarks Fixate® Superhold (INCI name=Polyacrylate-2 Crosspolymer), Fixate® Freestyle Polymer (INCI name=Acrylates crosspolymer-5 3), Carbopol® Aqua SF1 (INCI name=Acrylates copolymer) and Carbopol® Aqua SF2 (INCI name=Acrylates crosspolymer-4).

Preferably, the crosslinked copolymer is sold under the trademark Carbopol® Aqua SF1 (INCI name=Acrylates copolymer).

According to one embodiment, the crosslinked copolymer is chosen from crosslinked copolymers of acrylic or methacrylic acid and of alkyl acrylates comprising from 1 to 4 carbon atoms.

According to the invention, an emulsion according to the invention may comprise from 0.1% to 10% by weight, preferably from 0.5% to 8% by weight, and more preferably from 1% to 3% by weight of crosslinked polymer or crosslinked copolymer relative to the total weight of the emulsion.

The emulsions according to the invention may comprise a carbomer and a crosslinked copolymer sold under the trademark Carbopol® Aqua SF1 (INCI name=Acrylates copolymer).

Cationic Polymer

The fatty phase, in particular the dispersed fatty phase, comprises at least one cationic polymer.

According to one embodiment, the drops, and especially the shell of the drops, further comprise a cationic type polymer. They may also comprise several cationic type polymers. This cationic polymer is the one mentioned above which forms the shell by coacervation with the anionic polymer.

In the context of the present application, and unless otherwise stated, the term "cationic polymer" (or "cationic type polymer") is understood to mean a polymer having chemical functions of a cationic type. Reference is also made to cationic polyelectrolyte.

Preferably, the cationic polymer is lipophilic or fat-soluble.

In the context of the present application, and unless otherwise stated, the term "chemical function of the cationic type" is understood to mean a chemical function B capable of capturing a proton to give a function $BH^+$. According to the conditions of the medium in which it is located, the cationic type polymer therefore has chemical functions in form B, or in form $BH^+$, its conjugated acid.

As an example of chemical functions of the cationic type, mention may be made of the primary, secondary and tertiary amine functions that are optionally present in the form of ammonium cations.

An example of a cationic polymer that may be mentioned is any polymer formed by the polymerization of monomers at least a part of which carries chemical functions of the cationic type, such as primary, secondary or tertiary amine functions.

Such monomers are, for example, aziridine, or any ethylenically unsaturated monomer containing at least one primary, secondary or tertiary amine function.

Among the examples of cationic polymers suitable for the implementation of the invention, mention may be made of amodimethicone, derived from a silicone polymer (polydimethylsiloxane, also called dimethicone), modified by primary amine functions and secondary amine.

Mention may also be made of amodimethicone derivatives, for example copolymers of amodimethicone, aminopropyl dimethicone, and more generally linear or branched silicone polymers containing amine functional groups. The bis-isobutyl PEG-14/amodimethicone copolymer, Bis ($C_{13}$-$C_{15}$ Alkoxy) PG-Amodimethicone, Bis-Cetearyl Amodimethicone and bis-hydroxy/methoxy amodimethicone may be mentioned.

Mention may also be made of polysaccharide polymers comprising amine functions, such as chitosan or guar gum derivatives (hydroxypropyltrimonium guar chloride).

Mention may also be made of polypeptide-type polymers comprising amine functions, such as polylysine.

Mention may also be made of polyethyleneimine polymers comprising amine functional groups, such as linear or branched polyethyleneimine.

According to one embodiment, the drops, and in particular the shell of the drops, comprise a cationic polymer which is a silicone polymer modified with a primary, secondary or tertiary amine function, such as amodimethicone.

According to one embodiment, the drops, and in particular the shell of the drops, comprise amodimethicone.

According to a preferred embodiment, the amodimethicone does not contain cyclomethicone, such as, for example, cyclotetra-siloxane or cyclopentasiloxane.

According to one embodiment, the viscosity of the cationic polymer, and in particular of amodimethicone, ranges from 200 mPa·s to 50,000 mPa·s, preferably from 500 mPa·s to 10,000 mPa·s, and even more preferably 800 mPa·s to 4000 mPa·s as measured at 25° C.

According to a particularly preferred embodiment, the cationic polymer has the following formula (I):

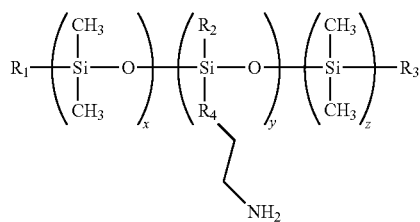

in which:
$R_1$, $R_2$ and $R_3$, independently of each other, represent OH or $CH_3$;
$R_4$ represents a group —$CH_2$— or a group —X—NH— in which X is a divalent alkylene radical in $C_3$ or $C_4$;
x is an integer between 10 and 5000, preferably between 30 and 1000, and more preferably between 80 and 300;
y is an integer between 2 and 1000, preferably between 4 and 100, and more preferably between 5 and 20; and
z is an integer between 0 and 10, preferably between 0 and 1, and better is equal to 1.

In formula (I) above, when $R_4$ is —X—NH—, X is attached to the silicon atom.

In the aforementioned formula (I), $R_1$, $R_2$ and $R_3$ are preferably $CH_3$.

In the aforementioned formula (I), $R_4$ is preferably —$(CH_2)_3$—NH—.

According to a particularly preferred embodiment, the cationic polymer has the following formula (I-1):

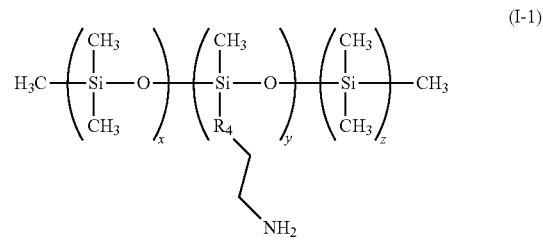

in which:
$R_4$ is as defined above, and is preferably a —$(CH_2)_3$—NH— group;
x is an integer between 80 and 300, preferably between 100 and 200;
y is an integer between 5 and 20, preferably between 5 and 15; and
z is an integer between 0 and 1, and preferably equal to 1.

According to one embodiment, in the aforementioned formula (I-1), $R_4$ is a —$(CH_2)_3$—NH— group, z is 1, x is in the range 80 to 300, and y is in the range 5 to 15.

According to one embodiment, in the aforementioned formula (I-1), $R_4$ is a —$(CH_2)_3$—NH— group, z is equal to 1, x is between 100 and 200, and y is between 5 and 15.

According to one embodiment, in the aforementioned formula (I-1), $R_4$ is a —$(CH_2)_3$—NH— group, z is equal to 1, x is between 100 and 150, and y is between 5 and 12.

According to one embodiment, the quantity of amine functional groups present in (or brought by) the cationic polymer, and especially in amodimethicone, is between 0.01 mmol and 12.3 mmol, preferably between 0.1 mmol and 8 mmol, more preferably between 0.5 mmol and 4 mmol, or even between 0.5 mmol and 2 mmol, per gram of cationic polymer.

In the context of the invention, and unless otherwise stated, the term "the quantity of amine functions present in (or provided by) the cationic polymer" is understood to mean the quantity of amine functions carried by the cationic polymer.

For obvious reasons, the amine functions provided by the cationic polymer in question are those capable of reacting with the anionic polymer, in particular with the carboxylic groups (or functions) carried by the anionic polymer. These are preferably amine functions present on the branched chains of the cationic polymer.

Thus, advantageously, at least 50%, preferably at least 60%, in particular at least 70%, better still at least 80%, more preferably at least 90%, and most preferably at least 99%, of the amine functions carried by the cationic polymer are capable of reacting with the anionic polymer, in particular with the carboxylic groups carried by the anionic polymer.

In order to ensure effective bridging between the amine functions of the cationic polymer and the carboxylic function(s) of the anionic polymer, and, as stated above, a cationic polymer according to the invention comprises at least two amine functional groups. In this respect and preferably, a cationic polymer according to the invention comprises at least two amine functions located on different branched chains of the cationic polymer. In other words, a cationic polymer according to the invention comprises at least two branched chains, which are identical or different, wherein each branched chain comprises at least one amine functional group capable of reacting with the anionic polymer, in particular with at least one carboxylic group carried by the anionic polymer.

According to one embodiment, the cationic polymer, and especially amodimethicone, has a viscosity of from 200 mPa·s to 50,000 mPa·s and/or the quantity of amine functions present in the cationic polymer is between 0.01 mmol and 12.3 mmol, preferably between 0.1 mmol and 10.0 mmol, more preferably between 0.5 mmol and 4.0 mmol, and in particular between 1.0 mmol and 3.0 mmol per gram of cationic polymer.

Preferably, the cationic polymer, and especially amodimethicone, has a viscosity of from 700 mPa·s to 4000 mPa·s and/or the quantity of amine functions present in the cationic polymer is between 0.5 mmol and 3.0 mmol per gram of the cationic polymer.

Method for Determining the Quantity of Amine Functions Present in the Cationic Polymer, Especially Amodimethicone The quantity of amine functional groups present in the cationic polymer may, in particular, be measured according to the following method:

Settings

Unless otherwise specified, perform the test described below under ambient conditions, i.e. ambient temperature (25° C.) and 30%-70% relative humidity.

Dry tris (hydroxymethyl) aminomethane (TRIS) (CAS No 77-86-1) at 110° C. for 2 hours minimum and cool over one week.

Method

Preparation of the Solvent Solution (i.e. Solution A)

Measure 1000 ml of HPLC grade toluene in an amber bottle.

Add 10 ml of distilled water.

Add 990 ml of isopropyl alcohol.

Close the bottle and gently mix the solution for about a minute.

This gives the solution A.

Verify that solution A is slightly acidic (pH~5) by adding 3 drops of bromcresol purple indicator solution to a 100 ml aliquot of solution A.

Stir for about 30 seconds.

The solvent solution should appear yellow/green after mixing.

Preparation of 0.5% Bromcresol Green Indicator Solution (i.e. Solution B)

Measure in a bottle 0.50±0.01 grams of a bromcresol green dye.

Add 100 ml of ethanol.

Close the bottle and shake vigorously.

This produces solution B.

Titration of a Solution of HCl (i.e. Solution C)

Measure an appropriate quantity in TRIS. Record the mass of TRIS M1.

NOTE: add about 0.2 grams of dried TRIS with 0.1 N HCl; add about 1.8 grams of dried TRIS with 1N HCl.

Add 100 ml of demineralized water.

Add 3 drops of solution B.

Stir for about 3 minutes.

NOTE: The TRIS solution should appear blue after shaking.

Position a 25 ml burette.

Fill the burette with a standard solution of HCl. Purge the top of the burette from the air by allowing about 1.0 ml of HCl to flow through the top of the burette.

The standard solution of HCl in the burette should be between 0.00-1.00 ml.

Record the volume of HCl in the burette V1.

Start the titration by adding the standard solution of HCl by adding 0.5 ml to the TRIS solution while stirring the TRIS solution with a magnetic stirrer.

Carefully approach the end point of the titration by slowly adding small drops of standard HCl solution to the TRIS solution until the color of the TRIS solution changes from blue to yellow and remains yellow for at least 60 seconds.

NOTE: The color of the TRIS solution may temporarily change from blue to green near where the titrant is added. As a titrant, the color change of the TRIS solution will become more dispersed and last longer. The titration is complete when the TRIS solution color turns yellow by adding the last drop of reagent and the color change persists for at least 60 seconds.

Record the final volume of HCl in the V2 burette.

Repeat until three successful titrations are completed.

Titration of the Cationic Polymer

Measure 0.05 grams to 5 grams of the cationic polymer in question, in particular amodimethicone, as a function of the amine content in the cationic polymer.

Record the mass of cationic polymer M2.

Add 50 ml of solution A.

NOTE: If the cationic polymer does not dissolve in solution A, first add isopropanol followed by toluene and water in appropriate ratio.

Add 3 drops of solution B.

This gives the solution D.

Mix the solution D for at least 5 minutes or until solution D appears homogeneous.

NOTE: Solution D should change from blue to green after shaking.

Position a 25 ml burette.

Fill the burette with a standard solution of HCl. Purge the top of the burette of the air by allowing about 1.0 ml of HCl to flow through the top of the burette.

The standard solution of HCl in the burette should be between 0.00-1.00 ml.

Record the volume of the standard HCl solution in the V3 burette.

Begin the titration by adding the standard solution of HCl to the solution D by additions of 0.5 ml while stirring the solution D with a magnetic stirrer.

Approach the titration endpoint with caution by slowly adding small drops of standard HCl solution until the color of Solution D changes from blue to yellow and remains yellow for at least 60 seconds.

NOTE: The color of solution D will temporarily change from blue to yellow or green near where the titrant is added. In some samples, the color may change from blue to purple to yellow. The titration is complete when the color of solution D turns yellow upon adding the last drop of reagent and the color change persists for at least 60 seconds.

Record the final volume of standard HCl solution in the burette as V4.

Calculations

Calculation of the normality of the standard solution of hydrochloric acid:

$$N = \frac{M_1}{(0.12114)(V_2 - V_1)}$$

N=normality of HCl, in N
M1=mass of TRIS, in grams
V1=initial volume of standard HCl solution in the burette, in mL
V2=final volume of standard HCl solution in the burette, in mL Calculation of the amine group content (in millimoles of amine/gram of cationic polymer)

$$\text{Amine} = \frac{N \times (V_4 - V_3)}{M_2}$$

M2=mass of the cationic polymer, in grams
V3=initial volume of standard HCl solution in the burette, in mL
V4=final volume of standard HCl solution in the burette, in mL
N=means the normality of the standard solution of HCl in the burette, in N Formulas Calculation of the normality of the standard solution of HCl (N):

$$N(\text{eq/L}) = (\text{grams of Tris})\left(\frac{1 \text{ mole } TRIS}{121.135 \text{ g } TRIS}\right) \times$$

$$\left(\frac{1 \text{ eq } TRIS}{1 \text{ mole } TRIS}\right) \times \left(\frac{1 \text{ eq HCl}}{1 \text{ eq } TRIS}\right) \times \left(\frac{1}{\text{mL HCl}}\right) \times \left(\frac{1000 \text{ mL}}{1 \text{ L}}\right)$$

Calculation of the amine content (in millimoles/gram of cationic polymer):

$$\text{Amine millimole/gram} = (\text{mL of HCl}) \times \left(\frac{\text{eq of HCl}}{\text{Lot HCl}}\right) \times \left(\frac{1}{\text{gram}}\right) \times$$

$$\left(\frac{1 \text{ mole Amine}}{1 \text{ eq of HCl}}\right) \times \left(\frac{1 \text{ L HCl}}{1000 \text{ mL HCl}}\right) \times \left(\frac{1000 \text{ mmole Amine}}{1 \text{ mole amine}}\right)$$

Method for Determining the Quantity of Amine Functions Provided by the Cationic Polymer, in Particular Amodimethicone, in the Fatty Phase Starting from a specific cationic polymer, persons skilled in the art are able to carry out the appropriate calculations to determine the required quantity of cationic polymer in question to meet the requirements in terms of the quantity of amine functions provided by the cationic polymer in the fatty phase as referred to in the present invention.

Mention may be made of the following calculation method:

$$Q = A \times T$$

where:
Q represents the quantity of amine functions provided by the cationic polymer in the fatty phase (in µmol/g),
A represents the weight percentage of the cationic polymer in question in the fatty phase, and
T represents the proportion of amine functions carried by the cationic polymer in question (in µmol/g of cationic polymer), in particular obtained by the method described above.

The cationic polymer according to the invention may be one of the following commercial products sold under the product names: CAS 3131 from Nusil, KF 8005 S or KF 8004 from Shin Etsu, sold under the trademark Silsoft® AX or SF 1708 from Momentive and DC 8500, DC 2-2078 or DC 2-8566 from Dow Corning.

The cationic polymer according to the invention may be an amodimethicone such as, for example, one of the following commercial products: CAS 3131 from Nusil, KF 8005 S or KF 8004 from Shin Etsu, SF 1708 from Momentive and DC 2-8566 from Dow Corning.

According to one embodiment, an amodimethicone according to the invention is distinct/different from an oil such as those described above and capable of composing the fatty phase of the drops of an emulsion according to the invention.

Advantageously, each drop of an emulsion according to the invention may comprise from 0.01% to 10%, preferably from 0.05% to 5% by weight of cationic polymer(s), in particular amodimethicone(s), relative to the total weight of the fatty phase.

According to the invention, the emulsion of the invention may comprise from 0.01% to 5%, preferably from 0.01% to 2%, and more preferably from 0.02% to 0.5% by weight of cationic polymer(s), especially amodimethicone(s), relative to the total weight of the emulsion. In particular, the above-mentioned emulsion may comprise from 0.020% to 0.1% by weight of cationic polymer(s) relative to the total weight of the emulsion.

Aqueous Phase

An emulsion according to the invention comprises an aqueous phase, in particular a continuous aqueous phase, preferably in the form of a gel.

In addition to the anionic polymer as defined above, the aqueous phase of the emulsions according to the invention comprises water.

In addition to distilled or deionized water, water suitable for the invention may also be natural spring water or floral water.

According to one embodiment, the mass percentage of water of the aqueous phase, in particular of the continuous aqueous phase, is at least 40%, and better still at least 50%, especially between 70% and 98%, preferentially between 75% and 95%, relative to the total mass of the aqueous phase.

An emulsion according to the invention of the oil-in-water type may comprise at least 20%, preferably at least 30%, in particular at least 40%, and better still at least 50% by weight of water relative to the total weight of the emulsion.

An emulsion according to the invention of the water-in-oil type may comprise less than 50%, preferably less than 40%, in particular less than 30%, better still less than 20%, or even less than 10%, by weight of water relative to the total weight of the emulsion.

Preferably, the emulsions according to the invention of the oil-in-water type comprise at least 75% by weight of aqueous phase.

The continuous aqueous phase of the emulsion according to the invention may further comprise at least one base. It may comprise a single base or a mixture of several different bases. The presence of at least one base in the aqueous continuous phase contributes, in particular, to enhancing the viscosity of the latter.

According to one embodiment, the base present in the aqueous continuous phase is a mineral base.

According to one embodiment, the mineral base is selected from the group consisting of alkali metal hydroxides and alkaline earth metal hydroxides.

Preferably, the mineral base is an alkali metal hydroxide, and especially NaOH.

According to one embodiment, the base present in the aqueous continuous phase is an organic base. Among organic bases, mention may be made, for example, of ammonia, pyridine, triethanolamine, aminomethylpropanol, or else triethylamine.

An oil-in-water type emulsion according to the invention may comprise from 0.01% to 10% by weight, preferably from 0.01% to 5% by weight, and more preferably from 0.02% to 1% by weight of base, preferably of mineral base, and in particular of NaOH, relative to the total weight of the emulsion.

Gelling Agent(s)

According to the fluidity of the emulsion that it is desired to obtain, it is possible to incorporate in the emulsion according to the invention one or more gelling agents that are different from the cationic and anionic polymers described above.

Thus, in an emulsion according to the invention, the aqueous phase may comprise at least one gelling agent and/or the fatty phase may comprise a gelling agent that is different from the anionic polymer and the cationic polymer.

Preferably, the aqueous phase, especially a continuous phase, may comprise at least one crosslinked copolymer as described above as the gelling agent, and in particular sold under the trademark Carbopol® Aqua SF1 (INCI name=Acrylates copolymer).

Additional Compound(s)

The emulsions of the invention may further comprise powders, flakes, dyes, preservatives, humectants, stabilizers, chelators, emollients, etc., or any usual cosmetic additive, and mixtures thereof.

The emulsions according to the invention may also comprise at least one active agent, preferably chosen from hydrating agents, healing agents, depigmenting agents, UV filters, desquamating agents, antioxidants, active agents stimulating the synthesis of dermal macromoleculars. and/or epidermal, dermodecontracting agents, antiperspirants, anti-aging agents, perfumes, and mixtures thereof.

According to one embodiment, an emulsion according to the invention is free of a perfuming agent.

Of course, those skilled in the art will take care to choose the additional compound(s) and/or their quantity as a function of the aqueous or fatty nature of the phase in question and/or in such a way that (i) the advantageous properties of an emulsion according to the invention, and (ii) the integrity of the drops forming the emulsion, are not or not substantially impaired by the addition envisaged. These adjustments are within the competence of persons skilled in the art.

According to one embodiment, the emulsions of the invention, in particular of the oil-in-water type, comprise glycerine. Preferably, the emulsions of the invention comprise at least 5% by weight of glycerine relative to the total weight of the emulsions. In fact, in addition to the texture, the emulsions according to the invention provide another advantage over "conventional" emulsions because they allow the use of glycerin, moreover in high levels.

They may, in particular, comprise glycerin in a content greater than or equal to 10%, greater than or equal to 20%, greater than or equal to 30%, greater than or equal to 40%, or even up to 50%, by weight, relative to the total weight of the emulsion.

For obvious reasons, glycerin is present in the aqueous phase of an emulsion according to the invention.

Preparation Method

The emulsions according to the invention may be prepared by different methods.

Thus, the emulsions according to the invention have the advantage of being able to be prepared according to a simple "non-microfluidic" method, i.e. by simple emulsification.

As in a conventional emulsion, an aqueous solution and a fatty solution are prepared separately. It is the stirring addition of the fatty phase in the aqueous phase which creates the direct emulsion.

The emulsions according to the invention may also be prepared according to a microfluidic method, in particular as described in the international applications WO 2012/120043 or WO 2015/055748, herein incorporated by reference.

According to this embodiment, the drops obtained by this microfluidic method have a uniform size distribution. Preferably, the dispersed phase of the invention consists of a population of monodisperse drops, in particular such that they have a mean diameter $\overline{D}$ of from 500 µm to 3000 µm and a coefficient of variation Cv of less than 10%, or even less than 3%.

In the context of the present description, the term "monodispersed drops" is understood to mean that the population of drops of the dispersed phase according to the invention has a uniform size distribution. Monodispersed drops have good monodispersity. Conversely, drops with poor monodispersity are said to be "polydispersed".

According to one embodiment, the average diameter D of the drops is, for example, measured by analysis of a photograph of a batch consisting of N drops, by means of image processing software (Image J). Typically, according to this method, the diameter is measured in pixels, then recorded in µm, depending on the size of the container containing the drops of the dispersion.

Preferably, the value of N is chosen to be greater than or equal to 30, so that this analysis reflects the drop diameter distribution of the emulsion in a statistically significant manner.

We measure the diameter Di of each drop, then we obtain the average diameter by calculating the arithmetic mean of these values:

$$\overline{D} = \frac{1}{N}\sum_{i=1}^{N} D_i$$

From these values of Di, we may also obtain the standard deviation a of the diameters of the drops of the dispersion:

$$\sigma = \sqrt{\frac{\sum_{i=1}^{N}(D_i - \overline{D})^2}{N}}$$

The standard deviation a of a dispersion reflects the distribution of the diameters Di of the drops of the dispersion around the average diameter $\overline{D}$.

Knowing the mean diameter $\overline{D}$ and the standard deviation a of a dispersion, one may determine that 95.4% of the drop population is found in the diameter range [$\overline{D}-2\sigma$, $\overline{D}+2\sigma$] and that 68.2% of the population is found in the interval [$\overline{D}-\sigma$; $\overline{D}+\sigma$].

To characterize the monodispersity of the dispersion according to this embodiment of the invention, the coefficient of variation may be calculated:

$$C_v = \frac{\sigma}{D}$$

This parameter reflects the distribution of the diameters of the drops as a function of the average diameter thereof.

The coefficient of variation Cv of the diameters of the drops according to this embodiment of the invention is less than 10%, preferably less than 5%, or even less than 3%.

Alternatively, the monodispersity may be demonstrated by placing an emulsion sample in a bottle of constant circular cross-section. Gentle stirring by rotating a quarter of a turn for half a second around the axis of symmetry passing through the bottle, followed by a rest of half a second is performed, before repeating the operation in the opposite direction, wherein this is performed four times in a row.

The drops of the dispersed phase are organized in a crystalline form when they are monodispersed. Thus, they form a stack in a repeating pattern in three dimensions. It is then possible to observe: a regular stack which indicates a good monodispersity, an irregular stack reflecting the polydispersity of the dispersion.

The presence, in the fatty phase, of solid fatty substance(s) at ambient temperature and pressure, as envisaged above, may necessitate adjustments in the method for preparing an emulsion according to the invention. In particular, the method for preparing such an emulsion according to the invention may comprise a heating step (between 40° C. and 150° C., in particular between 50° C. and 90° C.) of the fatty phase before mixing/contacting the fatty phase with the aqueous phase and, where appropriate and in the case of a "non-microfluidic" method as mentioned above, maintenance of this heating during stirring until the desired emulsion is obtained.

These adjustments are within the general competence of those skilled in the art.

In the case of an oil-in-water emulsion, the solutions (or fluids) used to constitute the continuous aqueous phase and the dispersed fatty phase are respectively designated External Fluid (FE) and Internal Fluid (FI).

In view of the foregoing, the fluid FI comprises at least a first precursor polymer of the coacervate, in particular a cationic polymer, and in particular amodimethicone and at least one oil and/or at least one solid fat at ambient temperature and pressure, in particular as defined above, and, additionally and optionally, at least one additional compound mentioned above.

The fluid FE comprises at least water and at least a second precursor polymer of the coacervate that is different from the first precursor polymer of the coacervate, in particular an anionic polymer, and in particular the carbomer, and, optionally, at least one additional aforementioned compound, or even a base, preservatives and/or other water-soluble products such as glycerin.

According to one embodiment, the method for preparing an oil-in-water type emulsion according to the invention comprises a drop-forming step comprising:

contacting a fluid FE and a fluid FI as defined above; and
the formation of drops of fatty phase, consisting of the fluid FI, dispersed in a continuous aqueous phase consisting of fluid FE, wherein the drops comprise a shell insulating the heart of the drops of the fatty phase of the dispersion.

According to one embodiment where the emulsion is prepared according to a microfluidic method, the step of contacting the fluid FE and the fluid FI as defined above may further comprise the presence of an intermediate fluid miscible with the FI fluid, as described in WO 2012/120043. This intermediate fluid is intended to form a film around the drop formed by the fluid FI in the fluid FE. Thus, the intermediate fluid delays the diffusion of the first precursor polymer coacervate present in the fluid FI until the intermediate fluid is mixed with the fluid FI and thus ensures the formation of very stable drops stabilized by a very thin shell without obstruction of the microfluidic device.

According to one embodiment, the drop formation step may further comprise a step of injecting a solution for increasing the viscosity of the continuous aqueous phase of the fluid FE. Preferably, the solution increasing the viscosity is aqueous. This solution for increasing the viscosity is typically injected into the aqueous external fluid FE after formation of the dispersion according to the invention, and thus after formation of the drops.

According to one embodiment, the solution for increasing the viscosity comprises a base, in particular an alkaline hydroxide, such as sodium hydroxide.

According to one embodiment, when the FI comprises at least one solid fat at room temperature and pressure as described above, the method for preparing a dispersion according to the invention may further comprise a step of heating the fluid FI, at a temperature of from 40° C. to 150° C., preferably from 50° C. to 90° C., prior to the aforementioned step of forming the drops, and therefore before mixing/contacting the fatty phase with the continuous aqueous phase.

This embodiment, in the case of a "non-microfluidic" method as mentioned above, may require the maintenance of this heating step after mixing/contacting the fatty phase with the continuous aqueous phase during stirring until the desired emulsion is obtained.

This embodiment, in the case where the emulsion is prepared according to a microfluidic method, is advantageous, in particular, in that it makes it possible to overcome the presence of the intermediate fluid described above.

According to this embodiment, the method of preparation may further comprise, between the heating step and the step of forming the drops, a step of lowering the temperature of the fluid FI, if necessary to room temperature.

Uses

Preferably, the emulsion according to the invention is directly usable at the end of the aforementioned preparation methods, as a composition, in particular a cosmetic composition. The emulsion when prepared according to the invention, is understood to refer to a microfluidic method as described above and that is also usable as a composition, in particular a cosmetic composition, after separation of the drops and redispersion of these in a second appropriate phase.

The invention also relates to the use of an emulsion according to the invention for the preparation of a composition, in particular a cosmetic composition.

The present invention thus also relates to a composition, in particular a cosmetic composition, comprising at least one dispersion according to the invention, in combination with a physiologically acceptable medium.

Preferably, a composition according to the invention does not comprise a surfactant.

The emulsions or compositions according to the invention may, in particular, be used in the cosmetics field.

They may comprise, in addition to the aforementioned ingredients, at least one physiologically acceptable medium.

The term "physiologically acceptable medium" is understood to mean a medium which is particularly suitable for the application of a composition of the invention to keratin materials, in particular the skin, the lips, the nails, the eyelashes or the eyebrows, and preferably the skin.

The physiologically acceptable medium is generally adapted to the nature of the support to which the composition is to be applied, as well as to the appearance under which the composition is to be packaged.

According to one embodiment, the physiologically acceptable medium is directly represented by the aqueous continuous phase as described above.

According to one embodiment, the emulsions or cosmetic compositions are used for the make-up and/or care of keratin materials, especially the skin.

The cosmetic compositions according to the invention may be care products, sun protection, cleaning (make-up removal), hygiene or make-up of the skin.

These compositions are therefore intended to be applied in particular to the skin.

Thus, the present invention also relates to the non-therapeutic cosmetic use of an emulsion or cosmetic composition mentioned above, as a make-up, for hygiene, cleaning and/or as a care product for keratin materials, in particular the skin.

According to one embodiment, the emulsions or compositions of the invention are in the form of a foundation, a make-up remover, or facial and/or body and/or hair, or anti-aging care, sun protection, oily skin care, whitening care, moisturizer, BB cream, tinted cream or foundation, facial cleanser and/or or body, a shower gel or a shampoo.

A care composition according to the invention may be, in particular, a solar composition, a care cream, a serum or a deodorant.

The emulsions or compositions according to the invention may be in various forms, in particular in the form of cream, balm, lotion, serum, gel, gel cream or mist.

When applied to a keratin material, in particular the skin, of an emulsion or a composition according to the invention, the drops of the emulsion destabilize very rapidly, typically under the shear generated by the fingers on the keratin material, without opposing resistance. This application behavior has the advantage of contrasting with the solid and granular visual appearance of the drops of the emulsion.

The present invention also relates to a non-therapeutic method for the cosmetic treatment of a keratin material, comprising a step of applying to the keratin material at least one emulsion or at least one layer of a cosmetic composition as defined above.

In particular, the present invention relates to a non-therapeutic method for the cosmetic treatment of the skin, comprising a step of applying to the skin at least one emulsion or at least one layer of a cosmetic composition as defined above.

The emulsions or compositions according to the invention advantageously have viscosities compatible with easy handling of the product obtained.

Throughout the description, including the claims, the phrase "comprising one" should be understood to be synonymous with "comprising at least one", unless the opposite is specified.

The expressions "between . . . and . . . ", "from . . . to . . . " and "from . . . until . . . " must be understood as being inclusive, unless otherwise specified.

The quantities of the ingredients in the examples are expressed as percentage by weight relative to the total weight of the composition, unless otherwise stated.

The examples which follow illustrate the present invention without limiting its scope.

EXAMPLES

The cationic polymers used in the following examples are the following amodimethicones:

| Amodimethicone | Viscosity (in mPa · s) | Quantity of amine functions (in mmol per gram of amodimethicone) |
|---|---|---|
| AM 1 (Nusil, CAS3131) | 1000 | 1.44 |
| AM 2 (Nusil) | 3850 | 0.72 |
| AM 3 (Nusil) | 900 | 0.71 |

AM1 and AM3 have a similar viscosity, but a number of different amine functions, while AM2 and AM3 have a similar quantity of amine functions but different viscosities.

Protocol

The emulsions of Examples 1 to 3 and 4 below, unless otherwise stated, are obtained by means of a preparation protocol implementing a microfluidic device, in particular as described in WO/2012/120043 and WO/2015/055748.

Example 1: Preparation of a Drop Dispersion

The compositions of the liquid phases for the preparation of the dispersions (comparative and according to the invention) are as follows:

The quantity of amodimethicone was varied in the dispersions prepared, thus leading to emulsions according to the invention (when the quantity of amine functional groups in the fatty phase is between 0.2 μmol and 10.5 μmol per gram of fatty phase) and comparative dispersions (ranges beyond that according to the invention).

| Fluid | Commercial name | INCI | Dispersion A % weight | Dispersion B % weight | Dispersion C % weight |
|---|---|---|---|---|---|
| OF | Osmosis water | Water | 96.495 | 96.495 | 96.495 |
| | Microcare PTG | Pentylenglycol | 2.5 | 2.5 | 2.5 |
| | Microcare PE | Phenoxyethanol | 1 | 1 | 1 |
| | Carbomer Tego ® 340FD | Carbomer | 0.25 | 0.25 | 0.25 |
| | Sodium hydroxyde pellets PRS codex | Sodium hydroxyde | 0.005 | 0.005 | 0.005 |
| | | Total | 100.000 | 100.000 | 100.000 |
| MF | Lanol 99 | Isononyl isononanoate | 100.000 | 100.000 | 100.000 |
| IF | Nusil CAS 3131 | Amodimethicone AM1 | 0.026 to 0.859 | | |

-continued

| Fluid | Commercial name | INCI | Dispersion A % weight | Dispersion B % weight | Dispersion C % weight |
|---|---|---|---|---|---|
| | | Amodimethicone AM2 | | 0.052 to 1.70 | |
| | | Amodimethicone AM3 | | | 0.0537 to 1.5 |
| | Lanol 99 | Isononyl isononanoate | sqf | sqf | sqf |
| | | Total | 100.000 | 100.000 | 100.000 |
| BF | Sodium hydroxide | Sodium hydroxide | 0.2 | 0.2 | 0.2 |
| | Osmosis water | Water | sqf | sqf | sqf |

*sqf: sufficient quantity for

The aqueous phases (OF) obtained have a viscosity of between 620 and 670 mPa·s (10 rpm) and a pH of between 4.60 and 4.75.

The phase rates used in the microfluidic device are as follows:

| Phase | Flow rates (mL/hr) |
|---|---|
| OF | 100 |
| MF | 3.2825 |
| IF | 9.8475 |
| BF* | 10 |

*Only for mechanical strength tests.

The geometry of the nozzle of the microfluidic device was fixed with the internal diameter of the stainless steel rod, 1 mm, and the internal diameter of the OF channel, 1.8 mm.

Example 2: Coalescence Test

Coalescence tests were carried out on the dispersions prepared in Example 1, comprising amodimethicones AM1 (dispersions A), AM2 (dispersions B) or AM3 (dispersions C).

The quantification of this coalescence parameter was performed by visual observation using a scoring system ranging from 0 to 4. The score 0 represents the absence of coalescence while the note 4 represents a very strong coalescence and the presence of drops having a diameter greater than 2 mm.

The rating scale used is as follows:

| Score | Rating criteria |
|---|---|
| 0 | No coalescence |
| 1 | 1 to 3 coalesced drops |
| 2 | 4 to 10 coalesced drops |
| 3 | More than 10 coalesced drops |
| 4 | Presence of large drops (diameter >2 mm) |

To represent the evolution of the coalescence, the average of the scores obtained during the 3 months of follow-up was represented according to the quantity of amine functions provided by the amodimethicone in the FI of the dispersions.

This quantity is expressed in µmol of amine per gram of fatty phase according to the following formula:

$$Q = A \times T$$

wherein:
Q represents the quantity of amine functions provided by the cationic polymer in the fatty phase (in µmol/g),
A represents the weight percentage of the cationic polymer considered in the fatty phase, and
T represents the rate of amine functions carried by the cationic polymer considered (in µmol/g of cationic polymer), in particular obtained by the method described above).

Figure 2:
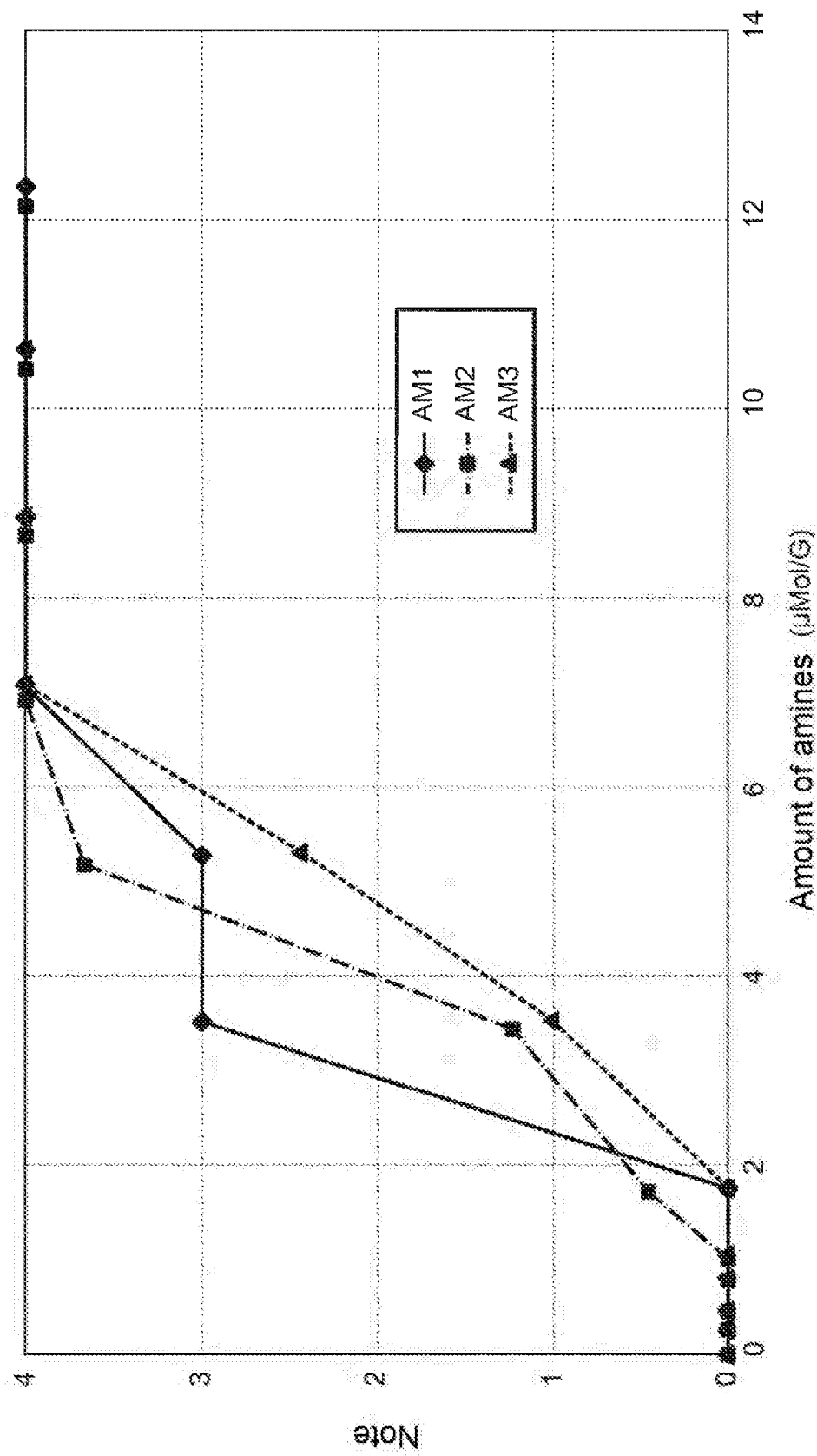

The results obtained at room temperature and 50° C. are shown in FIGS. 1 and 2.

FIG. 1 describes the evolution of the coalescence (average of the notes obtained during the 3 months of follow-up) as a function of the quantity of amine functions provided by the amodimethicone (AM1, AM2 or AM3) in the fatty phase at room temperature.

FIG. 2 describes the evolution of coalescence (mean of the scores obtained during the 3 months of follow-up) as a function of the quantity of amine functions provided by amodimethicone (AM1, AM2 or AM3) in the fatty phase at 50° C.

In FIGS. 1 and 2, the curves of the 3 amodimethicones tested (AM1, AM2 and AM3) have the same evolution. These amodimethicones therefore have a similar behavior in the face of coalescence. Thus, it may be deduced that the structural differences of amodimethicones do not seem to impact coalescence. On the other hand, it was observed that the coalescence is a function of the quantity of amine functions (provided by the amodimethicone) in the fatty phase.

Improved coalescences, i.e. low, or even zero, were observed in particular for dispersions whose quantity in amine functions (provided by amodimethicone) in the fatty phase is between 0.2 µmol and 7 µmol per gram of fatty phase (dispersions according to the invention), whatever the nature of the amodimethicone. These results advantageously demonstrate the stability of the emulsions according to the invention.

It has been shown that the coalescence is even lower, or even zero, for emulsions whose quantity in amine functions (provided by the amodimethicone) in the fatty phase is less than 7 µmol, or even less than 5 µmol, and in particular less than 3 µmol, per gram of fatty phase.

In particular, low or no coalescences were observed for dispersions whose quantity in amine functions (provided by amodimethicone) in the fatty phase is between 0.2 µmol and 5 µmol per gram of fatty phase, preferably between 0.2 µmol and 4 µmol. The best results are observed for dispersions whose quantity in amine functions (provided by amodimethicone) in the fatty phase is between 0.2 µmol and 3 µmol per gram of fatty phase, and especially between 0.2 µmol and 2 µmol.

Above 7 µmol per gram of fatty phase, the results show that coalescence is induced more significantly. This increase is even more marked for samples placed at 50° C. Thus, when the quantity of amine functions provided by the amodimethicone in the fatty phase is greater than 7 µmol, the dispersions have a greater coalescence, and therefore a lower stability compared to the dispersions according to the invention.

Example 3: Mechanical Strength Test

In the context of this example, the mechanical strength of the emulsions described in Example 1 above was evaluated using the following protocol: a glass pot of 4.5 cm in diameter and 7 cm in height containing the dispersions to a height of 50 mL, was positioned on a modular roller shaker (R2P-Wheaton). By imposing a rotation of the pot, the drops are subjected to a combination of deformations and relaxations. This offers both a simple shear but also the phenomena of compression and expansion.

The samples were subjected to a first cycle of 3 minutes at 6 rpm and then to a second cycle at 30 rpm of the same duration. After each cycle, a visual evaluation was performed on the samples with the following rating system: from 0 for no fragmentation, to 4 for a very large drop fragmentation. This test was performed 1 month after the production of the drops.

This rolling test made it possible to evaluate the shear strength of emulsion drops.

Figure 3:
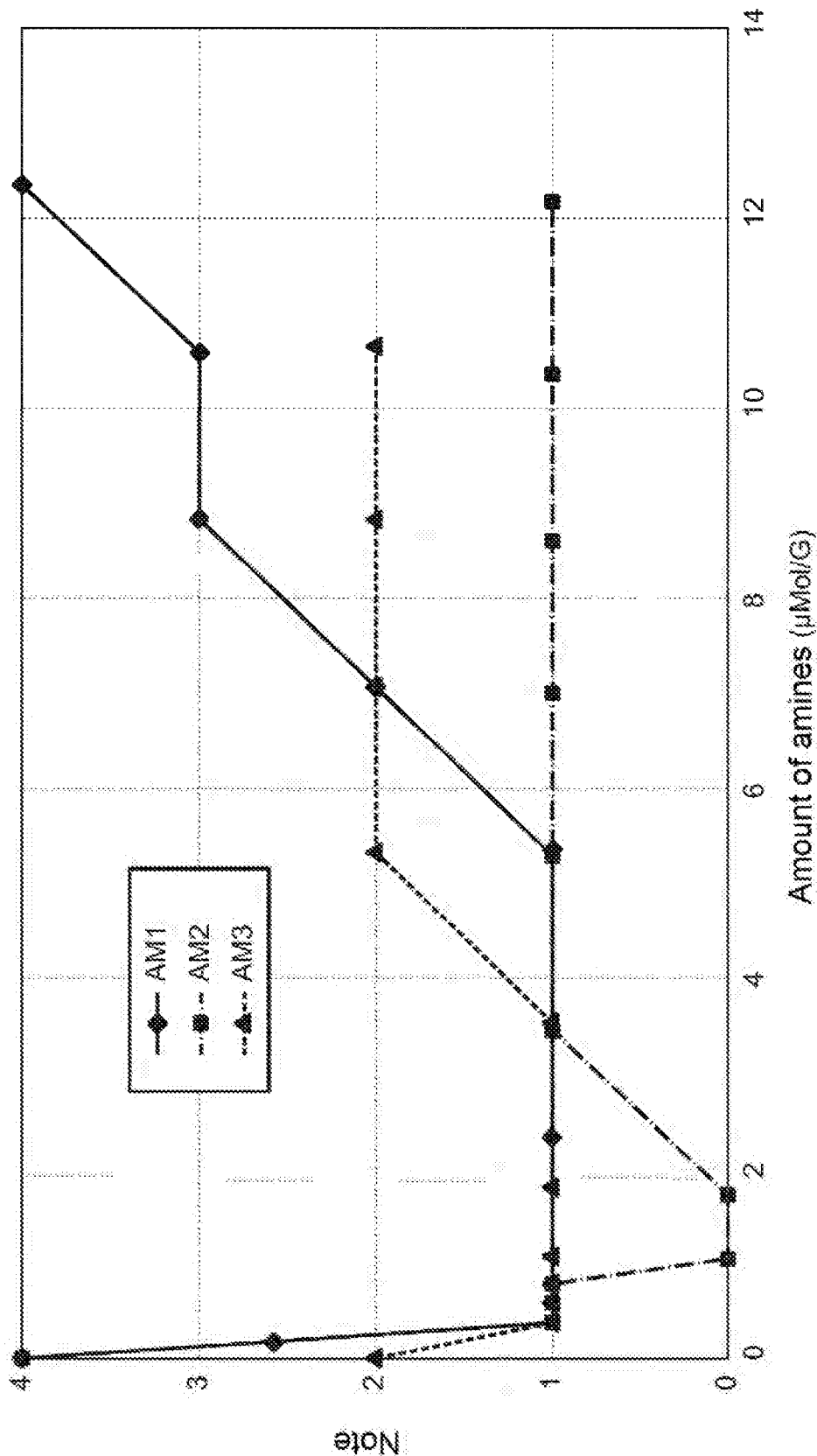
Figure 4:
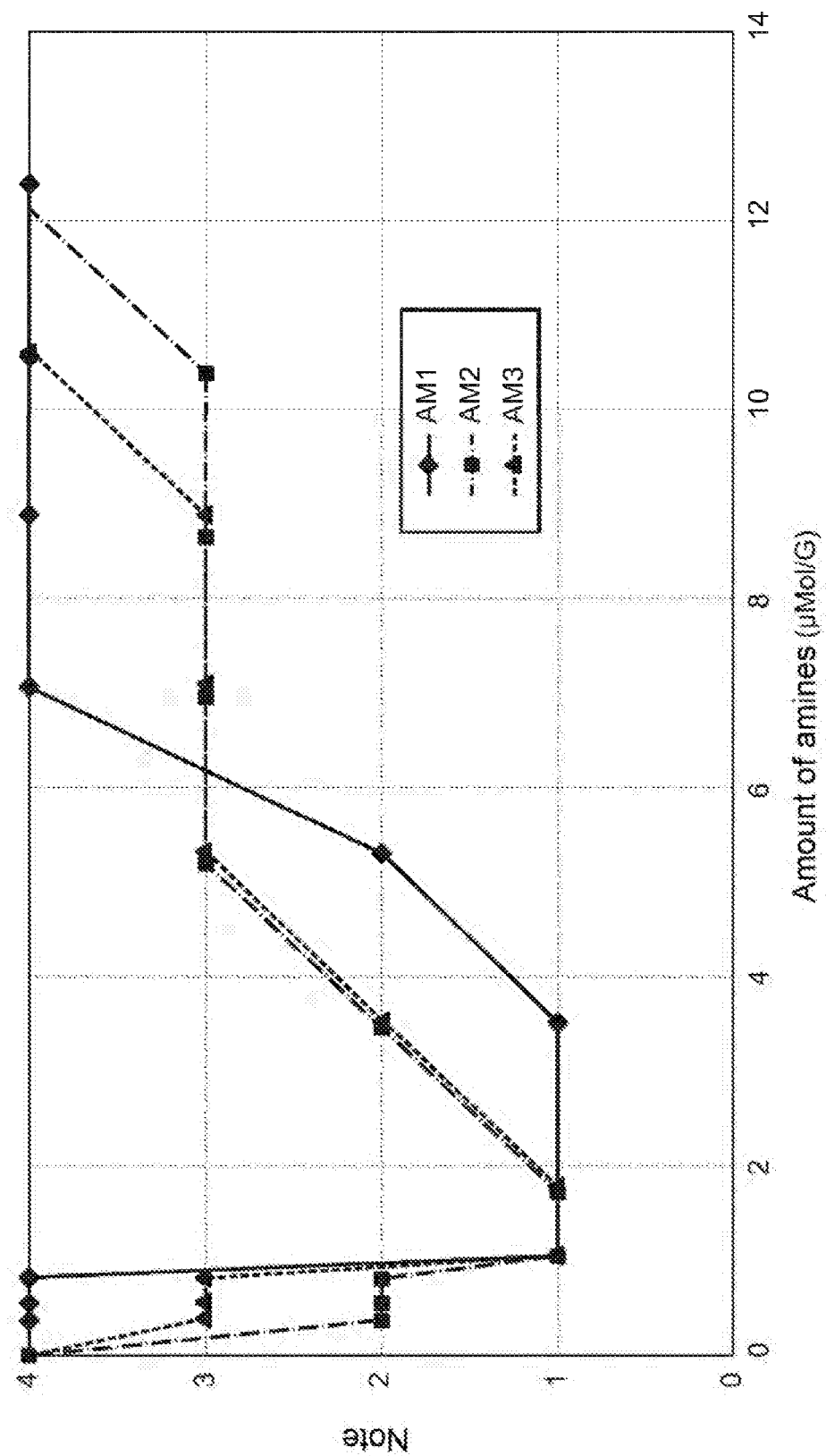

The results are shown in FIGS. 3 and 4 below.

FIG. 3 describes the evaluation of the mechanical resistance (visual rating) as a function of the quantity of amine functions provided by the amodimethicone (AM1, AM2 or AM3) in the fatty phase (in µmol per gram of fatty phase) at 6 rpm for 3 minutes.

FIG. 4 describes the evaluation of the mechanical resistance (visual rating) as a function of the quantity of amine functions provided by amodimethicone (AM1, AM2 or AM3) in the fatty phase (in µmol per gram of fatty phase) at 30 rpm for 3 minutes.

The results showed that, whatever the nature of the amodimethicone studied, the observed behavior is similar.

It has been shown that for quantities of amine functions provided by the amodimethicone, in the fatty phase, are too low, typically less than 0.2 µmol, wherein the mechanical strength of the drops is very low (a significant fragmentation is observed). Significant fragmentation of the drops is also observed for comparative dispersions comprising high quantities of amine functions, for example greater than 10.5 µmol, in the fatty phase.

Between these two extremes, an area was advantageously observed where the mechanical strength of the drops is satisfactory.

Despite good stability under static conditions, the dispersions obtained in the absence of amine have zero mechanical strength. Thus under flow, the stability of this sample is not acceptable. In an industrialization context, the emulsion is subjected to flow constraints which must not cause fragmentation of the drops.

However, it has been observed that the mechanical strength is improved by increasing the quantity of amine functions (provided by the amodimethicone) in the fatty phase.

Thus, the emulsions according to the invention comprising an quantity of amine functions provided by the amodimethicone in the fatty phase, of between 0.2 µmol and 10.5 µmol per gram of fatty phase, advantageously offer an improved resistance to fragmentation of the drops, which reflects a high mechanical strength for these emulsions.

This resistance to fragmentation of the drops is further improved for emulsions according to the invention comprising a quantity of amine functions provided by the amodimethicone in the fatty phase, of between 0.3 µmol and 7 µmol, preferably between 0.4 µmol and 5 µmol, and better still between 0.8 µmol and 2 µmol, per gram of fatty phase Example 4: Sparkling Balm for the Body Preparation Protocol (Non-Microfluidic Method)

In a beaker (1), weigh the osmosis water and the chelating agent(s) (in particular EDETA BD).

Place the beaker (1) under mechanical stirring with a deflocculating blade until homogenization.

Continue the stirring and add the anionic polymer(s) (especially the carbomer) in the beaker (1).

Leave the mixture obtained at rest for about 20 minutes (to ensure the hydration of the anionic polymer), then resume stirring until homogenization.

Weigh and add in the beaker (1) the gelling agent(s) of aqueous phase (including Aristoflex AVC, Sepimax zen).

If necessary, weigh and add 10% sodium hydroxide solution.

Stir until homogenization.

In another beaker (2), weigh the glycerin, if necessary with at least one gelling agent of aqueous phase.

Mix with a spatula to obtain a homogenous premix.

Add the premix (2) to the beaker (1).

When the solution obtained in the beaker (1) is homogeneous, heat the solution to 67° C.

In another beaker (3), weigh the cationic polymer (especially amodimethicone) and the isononyl isononanoate.

With magnetic stirring, heat the solution to 67° C. for about 5 minutes until homogenized.

Then, weigh any additional oils and/or solid fats still in the beaker (3).

Put everything under magnetic stirring, and heat to 67° C. for 10 minutes until homogenization.

When the solutions in the beakers (1) and (3) are at the given temperature (i.e. 67° C.), subject the solution of the beaker (1) to strong mechanical agitation.

Obtaining the emulsion then consists in adding the solution of the beaker (3) in the beaker (1) under this strong mechanical stirring.

Continue to stir for 15 to 20 minutes, then cool to 40° C. to 35° C.

In another beaker (4), add the preservative(s), especially phenoxyethanol (i.e. Microcare PE) and/or pentylene glycol (i.e. Microcare Emollient PTG).

Mix with a spatula to obtain a homogenous premix.

At 35° C., add the premix of the beaker (4) to the beaker (1).

When present, weigh and add the denatured alcohol (especially superfine 99 denat ethyl alcohol) into the beaker (1).

Leave to homogenize.

Weigh and add the cosmetic active and/or perfumes and/or coloring agents successively in the beaker (1).

Leave to homogenize.

Weigh and add a 10% soda solution in the beaker (1).

A body balm is prepared according to the protocol described above and comprises the following ingredients:

| Commercial designation | Supplier | INCI | % |
| --- | --- | --- | --- |
| Osmosis water | Capsum | AQUA | 52.460% |
| EDETA BD | BASF | DISODIUM EDTA | 0.030% |
| Microcare PE | Thor | PHENOXYETHANOL, AQUA | 0.800% |
| Microcare Emollient PTG | Thor | PENTYLENE GLYCOL, AQUA | 2.000% |
| Tego Carbomer 340 FD | Evonik | CARBOMER | 0.192% |
| Carbopol Ultrez 21 polymer | Lubrizol |  | 0.408% |
| Sepimax Zen | Seppic | POLYACRYLATE CROSSPOLYMER-6 | 0.250% |
| Glycerine codex (99%) | Interchimie | GLYCERIN | 20.000% |
| Zemea Propanediol | Dupont Tate & Lyle | PROPANEDIOL | 5.000% |
| Butylene glycol 1,3 | Interchimie | BUTYLENE GLYCOL | 5.000% |
| Solution soude 10% | Panreac | AQUA, SODIUM HYDROXYDE | 0.100% |
| Dub ININ | Nusil | ISONONYL ISONONANOATE | 2.000% |
| CAS-3131 | Nusil | AMODIMETHICONE | 0.020% |
| Dub PTB | Stéarinerie Dubois | PENTAERYTHRITYL TETRABEHENATE | 0.500% |
| Eutanol G |  |  | 1.000% |
| Lipex Shea Light | AAK | SHEA BUTTER ETHYL ESTERS | 1.000% |
| Plantec refined shea butter | CRM International | BUTYROSPERMUM PARKII | 0.500% |
| MOD | Gattefossé |  | 1.500% |
| Lipocire A | Gattefossé | TRIGLYCERIDES C10-18 | 1.000% |
| Floraesters 30 | Floratech | JOJOBA ESTERS | 0.500% |
| Lanette O OR | BASF | CETEARYL ALCOHOL | 1.000% |
| Dub VCl 10 | Stéarinerie Dubois | ISODECYL NEOPENTANOATE | 1.000% |
| Sensual Drop | Givaudan | FRAGRANCE | 0.300% |
| Sepimat SB | Seppic | METHYL MATHACRYLATE CROSSPOLYMER | 2.000% |
| Solution soude 10% | Panreac | AQUA, SODIUM HYDROXYDE | 0.900% |
| Prestige soft bronze | Eckart |  | 0.040% |
| Colorona Sun Gold | Merck |  | 0.100% |
| Sparkle MP-29 |  |  |  |
| Sunshine spectral gold | SunChemical |  | 0.400% |

Example 5: Anti-Aging Serum

Anti-aging serum with the following ingredients was prepared.

| Name | INCI name | % w/w PHASES | % w/w |
| --- | --- | --- | --- |
| AQUEOUS PHASE GEL | | | |
| Osmosis water | Water | 86.56 | 78.70 |
| Microcare PE | Phenoxyethanol | 0.88 | 0.80 |
| Microcare Emollient PTG | Pentylene glycol | 2.20 | 2.00 |
| Tego Carbomer 340FD | Carbomer | 0.27 | 0.25 |
| Rhodicare T | Xanthan gum | 0.11 | 0.10 |
| Phylcare Sodio Yaluronato XS | Sodium hyaluronate | 0.01 | 0.010 |
| Glycerine codex (99%) | Glycerin | 4.40 | 4.00 |
| Zemea | Propanediol | 5.50 | 5.00 |
| EDETA BD | Disodium EDTA | 0.03 | 0.030 |
| Solution 10% Sodium Hydroxide Pellets PRS codex | Aqua; sodium hydroxide | 0.04 | 0.038 |
| Total | | 100.00 | 90.93 |
| FATTY PHASE | | | |
| DUB ININ | Isononyl Isononanoate | 54.68 | 4.96 |
| KF-96A-50CS (PDMS 50 cSt) | Dimethicone | 44.68 | 4.06 |
| Ionol CP | BHT (hydroxytoluene butyl) | 0.45 | 0.040 |
| D&C Red N°17 K7007 | CI 26100 | 0.0013 | 0.00012 |
| Nusil CAS 3131 | Amodimethicone | 0.18 | 0.020 |
| Total | | 100.00 | 9.08 |
| Total | | | 100.00 |

The final composition comprises translucent pink fatty phase drops dispersed in a colorless aqueous gel.

The invention claimed is:

1. Emulsion comprising a continuous aqueous phase comprising an anionic polymer comprising at least one carboxylic acid group, and a dispersed fatty phase comprising a cationic polymer comprising at least two amine groups, and
   (i) wherein the fatty phase is in a form of drops surrounded by a shell formed of the anionic polymer comprising at least one carboxylic acid group and the cationic polymer comprising at least two amine groups; and
   (ii) wherein the total quantity of amine groups provided by the cationic polymer in the fatty phase is between 0.2 μmol and 7.0 μmol per gram of the fatty phase; and
   (iii) wherein said emulsion is kinetically stable at 25-50° C. for up to three months.

2. The emulsion according to claim 1, wherein the emulsion is an oil-in-water emulsion.

3. The emulsion of claim 1, wherein the cationic polymer is a silicone polymer modified with a primary, secondary or tertiary amine groups.

4. The emulsion of claim 1, wherein the cationic polymer has the following formula (I):

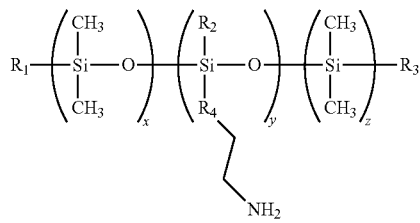

in which:
R$_1$, R$_2$ and R$_3$, independently of each other, represent OH or CH$_3$;
R$_4$ represents a group —CH$_2$— or a group —X—NH— in which X is a divalent alkylene radical having 3 or 4 carbon atoms;
x is an integer between 10 and 5000;
y is an integer between 2 and 1000; and
z is an integer between 0 and 10.

5. The emulsion of claim 4, wherein the cationic polymer has the following formula (I-1):

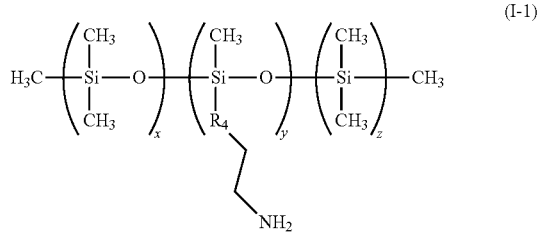

in which:
R$_4$ represents a group —CH$_2$— or a group —X—NH— in which X is a divalent alkylene radical having 3 or 4 carbon atoms;
x is an integer between 80 and 300;
y is an integer between 5 and 20; and
z is an integer between 0 and 1.

6. The emulsion of claim 1, wherein the quantity of amine groups present in the cationic polymer is between 0.01 mmol and 12.3 mmol per gram of the cationic polymer.

7. The emulsion of claim 1, wherein the fatty phase comprises from 0.01% to 10% by weight of the cationic polymer relative to the total weight of the fatty phase.

8. The emulsion of claim 1, wherein the anionic polymer is a carbomer or a crosslinked copolymer acrylates/C$_{10\text{-}30}$ alkyl acrylate.

9. The emulsion of claim 1, wherein the emulsion comprises from 0.01% to 5% by weight of anionic polymer relative to the total weight of the emulsion.

10. The emulsion of claim 2, comprising from 0.0001% to 50% by weight of oil(s) relative to the total weight of the emulsion.

11. The emulsion of claim 1, further comprising at least one active agent selected from the group consisting of hydrating agents, healing agents, depigmenting agents, UV filters, desquamating agents, antioxidants, stimulating active agents for the synthesis of dermal macromolecular agents, stimulating active agents for the synthesis of epidermal macromolecular agents, dermodecontracting agents, antiperspirant agents, anti-aging agents, perfuming agents, and mixtures thereof.

12. A cosmetic composition comprising the emulsion of claim 1.

13. A non-therapeutic method for a cosmetic treatment of a keratin material, comprising at least one step of applying to the keratin material the emulsion of claim 1.

14. A non-therapeutic method for a cosmetic treatment of a keratin material, comprising at least one step of applying to the keratin material the composition of claim 12.

15. The emulsion according to claim 1, wherein the total quantity amine groups provided by the cationic polymer in the fatty phase is calculated according to the formula:

$$Q = A \times T$$

where:
Q represents the quantity of amine groups provided by the cationic polymer in the fatty phase (in µmol/g),
A represents the weight percentage of the cationic polymer in the fatty phase, and
T represents the proportion of amine groups carried by the cationic polymer (in µmol/g of cationic polymer).

16. The emulsion according to claim 1, wherein the drops have a diameter of less than 2 mm after storage at 25-50° C. for up to three months.

17. The emulsion according to claim 1, wherein said emulsion is kinetically stable at 25-5O ° C. for up to three months, and wherein said emulsion undergoes less coalescence than an emulsion comprising a total quantity of amine groups provided by the cationic polymer in the fatty phase that is greater than 7.0 µmol per gram of the fatty phase.

* * * * *